US008965108B2

(12) United States Patent
Chabanas et al.

(10) Patent No.: US 8,965,108 B2
(45) Date of Patent: Feb. 24, 2015

(54) METHOD AND SYSTEM OF AUTOMATIC DETERMINATION OF GEOMETRIC ELEMENTS FROM A 3D MEDICAL IMAGE OF A BONE

(75) Inventors: Laurence Chabanas, Saint-Pierre-d'Allevard (FR); Stéphane Lavallee, Saint-Martin-d'Uriage (FR); Matthieu Nesme, Le Sappey (FR); Jonathan Schers, Grenoble (FR)

(73) Assignee: A2 Surgical, Le Mans (FR)

( * ) Notice: Subject to any disclaimer, the term of this patent is extended or adjusted under 35 U.S.C. 154(b) by 238 days.

(21) Appl. No.: 13/704,188

(22) PCT Filed: Jun. 16, 2011

(86) PCT No.: PCT/IB2011/001684
§ 371 (c)(1),
(2), (4) Date: Dec. 13, 2012

(87) PCT Pub. No.: WO2011/158114
PCT Pub. Date: Dec. 22, 2011

(65) Prior Publication Data
US 2013/0094732 A1     Apr. 18, 2013

Related U.S. Application Data

(60) Provisional application No. 61/355,203, filed on Jun. 16, 2010.

(51) Int. Cl.
*G06K 9/00* (2006.01)
*A61B 19/00* (2006.01)
(Continued)

(52) U.S. Cl.
CPC ............ *G06K 9/00362* (2013.01); *A61B 19/50* (2013.01); *G06K 9/6205* (2013.01);
(Continued)

(58) Field of Classification Search
USPC .......................................... 382/128–134, 154
See application file for complete search history.

(56) References Cited

U.S. PATENT DOCUMENTS 5,995,738 A  * 11/1999 DiGioia et al. ................. 703/11
6,853,741 B1   2/2005 Ruth et al.
(Continued)

FOREIGN PATENT DOCUMENTS

JP           2009273521           11/2009

OTHER PUBLICATIONS

Examination Report for Australian Patent No. 2011266777 dated Jul. 4, 2014, 4 pages.
(Continued)

*Primary Examiner* — Alex Liew
(74) *Attorney, Agent, or Firm* — David L. Fox; JL Salazar Law Firm

(57)    ABSTRACT

The invention relates to an automated method for precise determination of the head center and radius and the neck axis of an articulated bone from acquired 3D medical image of an articulation, comprising the following steps: i) determining, from a 3D image of the bone, an approximate sphere (SFO) of the head of the bone that substantially fits the spherical portion of the head of the bone; ii) constructing from the 3D image and the approximate sphere (SFO), a 3D surface model (S) of the bone; iii) determining, from the 3D surface model (S) and from the approximate sphere (SFO), an approximate neck axis (AXO) of the neck of the bone; iv) determining, from the 3D surface model (S) and the approximate sphere (SFO), a precise sphere (SF); v) determining, from the 3D surface model (S), the precise sphere (SF) and the approximate neck axis (AXO), a precise neck axis (AX1).

21 Claims, 19 Drawing Sheets

(51) Int. Cl.
  G06K 9/62      (2006.01)
  G06T 7/00     (2006.01)
  G06T 7/60     (2006.01)
  G06T 17/20    (2006.01)

(52) U.S. Cl.
  CPC ............. *G06T7/0042* (2013.01); *G06T 7/0083* (2013.01); *G06T 7/0089* (2013.01); *G06T 7/602* (2013.01); *G06T 7/606* (2013.01); *G06T 17/20* (2013.01); *A61B 2019/505* (2013.01); *G06T 2207/10072* (2013.01); *G06T 2207/30008* (2013.01)
  USPC .......................................... 382/154; 382/128

(56) References Cited

U.S. PATENT DOCUMENTS

| | | | |
|---|---|---|---|
| 7,672,709 | B2 | 3/2010 | Lavallee et al. |
| 2005/0143676 | A1 | 6/2005 | De Guise et al. |
| 2006/0204069 | A1* | 9/2006 | Le Bras et al. .................. 382/132 |
| 2006/0233430 | A1* | 10/2006 | Kimura .......................... 382/128 |
| 2007/0122233 | A1 | 5/2007 | Maier et al. |
| 2007/0195933 | A1 | 8/2007 | Bogojevic et al. |
| 2008/0086150 | A1 | 4/2008 | Mathis et al. |
| 2008/0177173 | A1 | 7/2008 | Deffenbaugh et al. |
| 2008/0214960 | A1 | 9/2008 | Hodgson et al. |
| 2008/0312663 | A1 | 12/2008 | Haimerl et al. |
| 2008/0319449 | A1 | 12/2008 | Tuma et al. |
| 2009/0017430 | A1 | 1/2009 | Muller-Daniels et al. |
| 2009/0089034 | A1 | 4/2009 | Penney et al. |
| 2009/0112214 | A1 | 4/2009 | Philippon et al. |
| 2009/0285465 | A1 | 11/2009 | Haimerl et al. |
| 2010/0049493 | A1 | 2/2010 | Haimerl |

OTHER PUBLICATIONS

Dudda M. et al, "Do Normal Radiographs Exclude Asphericity of the Femoral Head-Neck Junction?", Clin Orthop Relat Res (2009) 467:651-659.
Rakhra K.S. et al, "Comparison of MRI Alpha Angle Measurement Planes in Femoroacetabular Impingement", Clin Orthop Relat Res (2009) 467:660-665.
Kang et al, "Accurate simulation of hip joint range of motion", Computer Animation Conference—CA, pp. 215-219, 2002.
Brunner A. et al, "Evaluation of a Computed Tomography-Based Navigation System Prototype for Hip Arthroscopy in the Treatment of Femoroacetabular Cam Impingement", Arthroscopy: The Journal of Arthroscopic and Related Surgery, vol. 25, No. 4, Apr. 2009: pp. 382-391.
Arbabi E. et al, "A fast method for finding maximum range of motion in the hip joint", CAOS 2007, Heidelberg, Germany, p. 20-23.
Arbabi E. et al, "Penetration Depth Method—Novel Real-Time Strategy for Evaluating Femoroacetabular Impingement", Journal of Orthopaedic Research, vol. 28, Issue 7, pp. 880-886, Jul. 2010.
Dario P. et al, "A Novel Mechatronic Tool for Computer-Assisted Arthroscopy", IEEE Engineering in Medicine and Biology Society 2000;4(1):15-29.
Hodgson A.J. et al, "Computer-assisted femoral head resurfacing", Computer Aided Surgery, Sep./Nov. 2005; 10(5/6): 337-343.
Kendoff D. et al, "Feasibility of a navigated registration technique in FAI surgery", Archives of Orthopaedic and Trauma Surgery, vol. 131, No. 2, pp. 167-172, 2011.
Wengert C. et al, "Markerless Endoscopic Registration and Referencing", Med Image Comput Comput Assist Interv. 2006;9(Pt 1):816-23.
Monahan E. et al, "Computer-aided navigation for arthroscopic hip surgery using encoder linkages for position tracking", Int J Med Robotics Comput Assist Surg 2006; 2: 271-278.
Monahan E. et al, "A study of user performance employing a computer-aided navigation system for arthroscopic hip surgery", Int J CARS (2007) 2:245-252.
Charbonnier C. et al, "Motion study of the hip joint in extreme postures", The Visual Computer, vol. 25, No. 9, pp. 873-882, 2009.
Gilles B. et al, "MRI-based Assessment of Hip Joint Translations", J Biomech, vol. 42, Jun. 2009.
Murphy S.B. et al, "Arthroscopic percutaneous computer assisted FAI relief using a new method of CT-fluoro registration", Computer-Assisted Orthopedic Surgery—International, 2007.
Barrett A.R.W et al, "Preoperative planning and intraoperative guidance for accurate computer-assisted minimally invasive hip resurfacing surgery", Proc. IMechE vol. 220 Part H, 2006.
Puls M. et al, "Simulation of Hip Motion for Impingement Detection: A Comparison of Four Strategies", Journal of Biomechanics 41(S1), 16th ESB Congress, Oral Presentations, Tuesday Jul. 8, 2008.
Cai D. et al, "Rapid Impingement Detection System with Uniform Sampling for Ball-and-Socket Joint", Workshop on 3D Physiological Human, Zermatt, Switzerland, Dec. 1-4, 2008.
Tannast M. et al, << Computer-assisted Simulation of Femoroacetabular Impingement Surgery >>, in JB Stiehl, WH Konermann, RG Haaker, AM DiGioia (eds.): "Navigation and MIS in Orthopaedic Surgery", Berlin, Heidelberg, New York: Springer-Verlag. pp. 448-455, 2006.
Tannast M. et al, "Noninvasive three-dimensional assessment of femoroacetabular impingement", Journal of Orthopedic Research, Jan. 2007.
Wu C., "3D Reconstruction and Tracking of Anatomical Structures from Endoscopic Images", Thesis, 2009.
Charbonnier C. et al, "Virtual Hip Joint: from Computer Graphics to Computer-Assisted Diagnosis", Eurographics 2009, Mar. 30-Apr. 3, Munich, Germany.
Zaragoza E.J., "3D CT and the Imaging Approach to Femoroacetabular Impingement Syndrome", Section 4, Orthopedic Imaging, TeraRecon Clinical Case Studies—vol. 1, pp. 143-150.
Cerveri P et al: "Automated method for Computing the morphological and clinical parameters of the proximal femur using heuristic modeling techniques", Annals of Biomedical Engineering, May 2010 Springer Netherlands NLD, vol. 38, No. 5, May 2010, pp. 1752-1766, XP002663907.
Kang Y et al: "A New Accurate and Precise 3-D Segmentation Method for Skeletal Structures in Volumetric CT Data", IEEE Transactions on Medical Imaging, IEEE Service Center, Piscataway, N J, US, vol. 22, No. 5, May 1, 2003, pp. 586-598, XP001164803, ISSN: 0278-0062, D0I: 10.1109/TMI.2003.812265 pp. 586-587, 592-593.
Xiao Dong et al: "Determining Geometrical Parameters by Particle Filter for Automatic Reconstruction of Surface Model of Proximal Femur from Biplanar Calibrated Fluoroscopic Images", Contr0l, Automati0n, Robotics and Vision, 2006. ICARCV '06. 9th Internati0nal Conference on, IEEE, PI, Dec. 1, 2006, pp. 1-6, XP031103357.
Jun Y et al: "Design of patient-specific hip implants based on the 3D geometry of the human femur", Advances in Engineering Software, Elsevier Science, Oxford, GB, vol. 41, No. 4, Apr. 1, 2010, pp. 537-547, XP026903755.
June Sic Kim et al: "A new measurement method of femoral anteversion based on the3D modeling", Proceedings of the 19th Annual International Conference of the IEEE Engineering in Medicine and Biology Society. Magnificent Milestones and Emerging Opportunities in Medical Engineering (CAT. N0.97CH36136) IEEE ISBN: 0-7803-4262-3Piscataway, NJ, USA, vol. 1, 1997, pp. 418-421 vol. 1, XP002663908.
Heinrich M. Overhoff et al: "Automatic détermination of the newborn's fémoral head from three-dimensional ultrasound image data" In: "CVRMed-MRCAS'97",Jan. 1, 1997, Springer-Verlag, Berlin/Heidelberg, XP55012578, vol. 1205, pp. 545-556.
Khanmohammadi M et al: "A hybrid technique for thickness-map visualization of the hip cartilages in MRI", I EI CE Transactions on Information and Systems IEICE Japan, vol. E92-D, No. 11, Nov. 2009, pp. 2253-2263, XP002680122.

(56) References Cited

OTHER PUBLICATIONS

Gonzalez, Rafaël C, Richard E. Woods: "Digital Image Processing, Second Edition",2002, Prentice Hall, Inc., Upper Saddle River, New Jersey 07458, XP002680123, pp. 587-590.

Ballard D H: "Generalizing the Hough Transform to detect arbitrary shapes", Pattern Recognition, Elsevier, GB, vol. 13, No. 2, Jan. 1, 1981, pp. 111-122, XP002195911, ISSN: 0031-3203, D0I: 10.1016/0031-3203(81)90009-1 the whole document.

Weiwei Song et al: "Automatic Measurement of Morphological Parameters of Hip Joint of Morphological Parameters of Hip Joint from CT Images", Bioinformatics and Biomedical Engineering, 2008. ICBBE 2008. The 2nd International Conference on, IEEE, Piscataway, NJ, USA, May 16, 2008, pp. 2382-2385, XP031267814, ISBN: 978-1-4244-1747-6 p. 2384—left-hand column.

Nötzli et al, "The Contour of the Femoral Head-Neck Junction as a Predictor for the Risk of Anterior Impingement," Journal of Bone and Joint Surgery (BR), vol. 84-B, No. 4, May 2002, pp. 556-560.

Ito et al, "Femoracetabular Impingement and the Cam-Effect," Journal of Bone and Joint Surgery [Br], vol. 83-B, No. 2, Mar. 2001, pp. 171-176.

Pfirrmann Christian W.A. et al, "Cam and Pincer Femoroactabular Impingement : Characteristic MR Arthrographic Findings in 50 Patients", Radiology, Sep. 2006 Lnkd—Pubmed 16857978, vol. 240, n° 3, Sep. 2006 (2006-2009), pp. 778-785, XP002665712.

International Search Report for International Application No. PCT/IB2011/001684, mailed Sep. 3, 2012.

Examination Report for European Patent Application No. 11768076.9 dated Dec. 6, 2012, 8 pages.

\* cited by examiner

METHOD AND SYSTEM OF AUTOMATIC DETERMINATION OF GEOMETRIC ELEMENTS FROM A 3D MEDICAL IMAGE OF A BONE

TECHNICAL FIELD

The invention relates to the field of computer assisted surgery, and more particularly to a method and a system of determination of geometric elements from 3D medical image of a bone.

BACKGROUND OF THE INVENTION

Articulations of the human body are often very complex systems and no precise generic model exists to capture all the variability from one articulation to another. It is therefore necessary to use specific medical images or collection of digital patient data in order to get relevant information to develop techniques, devices and methods that will facilitate a treatment or a diagnosis. The present text focuses on the hip articulation between the acetabulum and the proximal femur although it can be easily extended to other articulations such as shoulder for example.

Structural abnormalities in the morphology of the hip can limit motion and result in repetitive impact of the proximal femoral neck against the acetabular labrum and its adjacent cartilage. Femoro Acetabular Impingement (FAI) is a pathology that can result from a decreased femoral head-neck offset (cam effect), an overgrowth of the bony acetabulum (pincer effect), excessive acetabular retroversion or excessive femoral anteversion, or a combination of these deformities. The cam impingement is generally characterized by a bone overgrowth located at the antero-superior aspect of the femur head-neck junction, which destructures the spherical shape of the femur head. The pincer impingement is generally characterized by an overcoverage located at the anterior aspect of the acetabulum rim. However, the correct and full diagnosis of this pathology is not easy to determine, especially when dealing with subtle deformities.

Standard radiographic X-rays are used for the initial diagnosis and then three dimensional (3D) Computed Tomography (CT) scans or Magnetic Resonance Imaging (MRI) exams are generally performed in case of suspected FAI pathology. It is known in the clinical literature to produce reformatted slices from 3D medical image volume, to create two dimensional (2D) image slices in different orientation in order to increase the chance of detecting bone deformation.

Especially in cases of FAI, it is known to reconstruct a pseudo axial slice passing through the middle of the neck axis and to characterize the loss sphericity of the femoral head by measuring an angle constructed from the neck axis and a radius of a circle fitted to the femoral head passing at the location where the bone surface quits the contour of the circle (definition of so-called "alpha angle" by Nötzli et al, in Journal of Bone and Joint Surgery, Volume 84-B, No. 4, May 2002, pages 556-560).

It is also known to create radial reformatted slices, by rotating the reformatting image plane along the neck axis at regular angular intervals, thus enabling the characterization of the bone deformation at several locations around the head-neck junction (Ito et al, in Journal of Bone and Joint Surgery [Br], Volume 83-B, No. 2, March 2001, pages 171-176).

Thus the alpha angle measurement as defined by Nötzli et al is also known to have been extended to a series of radial reformatted slices (Pfirrmann et al, in Radiology, Volume 240, No. 3, September 2006, pages 778-785).

Another important measurement is the orientation of the femoral neck, especially the version of the neck which is measured relatively to the knee rotation axis. This measurement is usually performed by measuring independently the orientation of the posterior condyles and the neck orientation in axial slices of the 3D image volume, and then recomputing from these two measures, a femoral neck version. The final neck version measurement thus being a combination of two measurements, only taking two dimensions into account, not reflecting true 3D orientation.

However, such processing of the 3D image remains a laborious manual task, comprising manual identification of the neck axis and manual fitting of a circle to the head of the bone in several 2D images, which cannot ensure accuracy and reproducibility, and can potentially mislead the diagnosis or the surgical indication.

The surgical treatment of FAI aiming at restoring a normal spherical shape to the femur head at the level of the bony cam lesion on the head neck-junction, it is crucial to have analysed and characterized as precisely as possible the location and the extent of the lesion. Moreover, as the surgeon will be addressing a 3D problem in the operating room, it is most important that the problem has been properly analysed in actual 3D and not only from sets of 2D slices.

From the issues described above, it can be easily understood that new specific methods are needed to answer the problems of bone deformation analysis.

The specific problem addressed by the invention is the difficulty to identify precisely and in an automatic manner critical anatomical elements of the femur anatomy in the pre-operative 3D medical image of the patient.

SUMMARY OF THE INVENTION

One object of the invention is an automated method for precise determination of the head center and radius and the neck axis of an articulated bone from acquired 3D medical image of an articulation, the articulation comprising two bones one of which is said bone with a head and a neck, the method comprising the following steps:

[a] determining automatically, from a 3D image of the bone having a head and a neck, an approximate sphere of the head of the bone defined by an approximate head center and an approximate radius, that substantially fits the spherical portion of the head of the bone;

[b] constructing automatically from the 3D image and from the approximate sphere of the head of the bone, a 3D surface model of the bone;

[c] determining automatically, from the 3D surface model of the bone and from the approximate sphere of the head of the bone, an approximate neck axis of the neck of the bone;

[d] determining automatically, from the 3D surface model and from the approximate sphere of the head of the bone, a precise sphere defined by a precise head center and a precise radius of the head of the bone;

[e] determining automatically, from the 3D surface model, from the precise sphere of the head and from the approximate neck axis, a precise neck axis.

The step of determining the approximate sphere advantageously comprises the following steps:

step a: defining from the 3D image of the bone having a head and a neck and from a threshold level which identifies level of cortical bone in medical images, a set of 3D connected components belonging to bone elements, and labelling these connected components with the bone of the articulation they belong to, in order to identify the 3D connected components belonging to the bone with a head and a neck;

step b: determining from said 3D connected components, said approximate sphere of the head of the bone that substantially fits the spherical portion of the head of the bone.

Preferably, step a) is carried out by an automatic computation comprising the following steps:
  [a] determining the lateral-medial, inferior-superior and anterior-posterior orientations of the bone comprising a head and a neck from the knowledge of the orientation of the 3D image;
  [b] computing the 3D connected components for a high threshold level by applying standard thresholding and connecting operators;
  [c] labelling the connected 2D component detected in the most inferior slice of the 3D image as belonging to the bone comprising a head and a neck;
  [d] propagating the label of the connected 2D component in the most inferior slice, to the 3D connected component containing the 2D component.

According to a first embodiment of the invention, step b) is carried out by an automatic computation determining amongst candidate points in the 3D image, the point yielding the greatest spherical score, the spherical score being a ratio representing the likelihood of the candidate point to be the center of a sphere fitting the head portion of the bone, the spherical score also defining the radius value associated with the center.

Preferably, the spherical score is computed by the following steps:
  [a] drawing a set of straight lines, each straight line diametrically extending from the approximate head center;
  [b] for each straight line, determining a pair of two intersection points positioned where the straight line intersects the 3D connected components of the bone with a head and a neck;
  [c] sorting all pairs of two intersection points into radius intervals depending on the distance separating the two intersection points of the pairs;
  [d] for each radius interval, counting the number of pairs in the radius interval;
  [e] determining the spherical score for the candidate point as the ratio between the greatest number of pairs amongst all radius intervals and the total number of straight lines in the set of straight lines.

According to another embodiment of the invention, step b) is carried out by an automatic computation comprising the following steps:
  [a] determining a 4D Hough space in the space of spheres determined by 4 parameters defining a head center and a radius, and applying the associated 4D Hough transform to the 3D connected components of the bone with a head and a neck, thus computing a weight for each point of the 4D Hough space;
  [b] determining the approximate sphere as the point in the 4D Hough space with heaviest weight.

According to an advantageous embodiment of the invention, the volume in which the approximate head center is searched for is reduced from the whole 3D connected components of the bone with a head and a neck to a portion of those 3D connected components, using a priori knowledge of the bone anatomy, and by applying a method comprising the following steps:
  [a] determining a bounding box of the 3D connected components of the bone with a head and a neck;
  [b] splitting the bounding box of the 3D connected components in two parts by an antero-posterior plane passing through the middle of the bounding box, and keeping only the portion of the 3D components contained in the medial hemi-bounding box;
  [c] splitting the medial hemi-bounding box in two subparts by an infero-superior plane passing through the middle of the medial hemi-bounding box, and keeping only the portion of the 3D components contained in the superior medial hemi-bounding box;
  [d] computing an antero-posterior plane passing through the middle of the superior medial hemi-bounding box;
  [e] computing spherical scores or 4D Hough transform respectively only along the segment passing through the middle of the antero-posterior plane, bounded by the superior medical hemi-bounding box.

In addition, the user may be asked to validate the resulting approximate sphere and, in case of failure of the automatic determination of a valid approximate sphere, step b) is carried out manually by designating in two orthogonal 2D slices selected in the 3D image of the bone an approximate head center point and drawing approximate circles over the head contours to determine an approximate sphere radius.

The step of constructing the 3D surface model of the bone may be carried out automatically by applying standard surface generation operators from said segmented 3D connected components.

If the used threshold is not differentiating enough to separate the 3D connected components of the bone with a head and a neck from the other bone of the articulation, the approximate sphere of the head of the bone may be used to force the segmentation and the separation of the 3D connected components of the bone with a head and a neck from the other bone of the articulation before the generation of said 3D surface model, and the approximate sphere surface is then used to complete generated said 3D surface model at the location of forced separation of the 3D connected components.

According to an embodiment of the invention, the step of determining the approximate neck axis is carried out by an automatic computation comprising the following steps:
  [A] tracing a defined number of hemi-lines, at regular intervals, from the approximate head center and in the directions contained in an inferior and lateral quarter of space of the 3D image, limited by a superior plane and a medial plane passing through the approximate head center;
  [B] determining for each hemi-line, a pair of intersecting points as the intersection of the hemi-line with the approximate sphere and with the 3D surface model of the bone;
  [C] selecting pairs of intersecting points whose relative distance is below a defined threshold and thus defining from the selected pairs of points, a 3D curve along the neck from the intersection points corresponding to the intersection of the hemi-lines with the 3D surface model of the bone;
  [D] computing a least-square plane from the points defining the 3D curve; the approximate neck axis being determined as the axis orthogonal to the least-square plane, passing through the approximate head center.

According to another embodiment of the invention, the step of determining the approximate neck axis is carried out by an automatic computation comprising the following steps:
  [A] tracing a defined number of hemi-lines, at regular intervals, from the approximate head center and in the directions contained in an inferior and lateral quarter of space of the 3D image, limited by a superior plane and a medial plane passing through the approximate head center;

[B] determining for each hemi-line, an intersecting point as the intersection of the hemi-line with the 3D surface model of the bone, and selecting hemi-lines for which the distance between the approximate head center and the intersecting points is the longest, within a defined threshold;

[C] computing for each selected hemi-line, radial planes rotating along the hemi-line at regular angulation interval, and computing the intersection curve of the 3D surface model of the bone and each radial plane;

[D] determining for each selected hemi-line, for each radial plane, a segment on the hemi-line by a minimum and a maximum distance from the approximate head center bounding the research area to the neck portion; and computing maximal distances from the segment to the intersection curve on both sides of the segment; the approximate neck axis being determined by the hemi-line associated with the smallest of the maximal distances.

Advantageously, the user is asked to validate the resulting approximate neck axis and, in case of failure of the automatic determination of a valid approximate neck axis, the determination of the neck axis is carried out manually by drawing lines approximating the neck axis in two orthogonal 2D slices selected in the 3D image of the bone.

The step of defining the precise sphere may be carried out by automatic computation of the following steps:

[A] determining a spherical portion of the head surface defined by the approximate sphere and a plane orthogonal to the approximate neck axis and comprising the approximate head center, the spherical portion being opposite the neck with respect to the plane orthogonal to the approximate neck axis;

[B] determining a set of hemi-lines extending from the approximate head center, in the spherical portion of the head;

[C] determining a set of intersecting points on the 3D surface model of the bone, each intersecting point corresponding to the intersection between a hemi-line and the 3D surface model;

[D] fitting a precise sphere to the set of intersecting points by a least square method; the center of the precise sphere being the precise head center and the radius of the precise sphere being the precise radius of the head of the bone.

The user may be asked to validate the resulting precise sphere and, in case of failure of the automatic determination of a valid precise sphere, the determination of the precise sphere is carried out manually by designating in two orthogonal 2D slices selected in the 3D image of the bone a precise head center point and drawing precise circles over the head contours to determine a precise sphere radius.

According to an embodiment of the invention, the step of defining the precise neck axis is carried out automatically by the following steps:

i) determining a 3D neck minimal curve on the 3D surface model of the neck portion of the bone;

ii) determining a least squares fitting plane to the 3D neck minimal curve;

iii) computing the orthogonal direction to the least squares fitting plane as the direction of the precise neck axis;

iv) computing the center of the projection of the 3D neck minimal curve on the least squares fitting plane as a point of the precise neck axis.

The 3D neck minimal curve may be determined by carrying automatically the following steps:

i) computing radial planes rotating along the approximate neck axis at regular angulation interval, and computing the intersection curve of the 3D surface model of the bone and each radial plane;

ii) determining for each radial plane, the minimum distances between the approximate neck axis and the intersection curve on both sides of the neck axis, and thus determining a pair of points on the 3D surface model; the set of pairs of points from all radial planes defining a minimal 3D curve on the 3D surface model of the neck portion of the bone;

The 3D neck minimal curve may further be determined by locally adjusting the 3D location of the points defining the 3D neck minimal curve comprising the following steps carried out automatically:

i) creating an energy function connecting contiguous points of the 3D neck minimal curve, as a sum of distance between contiguous points;

ii) minimizing the energy function by minimizing the distance between contiguous points.

According to another embodiment of the invention, the step of defining the precise neck axis is carried out automatically by the following steps:

i) computing the sphere intersection curves of the 3D surface model and a set of spheres centered on the precise head center and with increasing radius, starting from the precise radius of the head of the bone to a defined maximum radius;

ii) computing for each sphere intersection curve, a plane orthogonal to the line passing though the head center and the barycentre of the intersection curve;

iii) computing further a plane intersection curve of the 3D surface model and the orthogonal planes, and computing the barycentre of the plane intersection curve;

iv) computing a least square fitting line, fitting the set of barycentre points from the set of plane intersection curves, and the precise head center; the fitting line determining the precise neck axis.

The method may further comprise an automatic additional adjustment of the precise neck axis, computed by the following steps:

i) computing a radial frontal plane passing through the precise neck axis and the knee center point;

ii) adjusting the precise neck axis in the radial frontal plane so that the adjusted neck axis passes through the middle of the minimal segment joining two opposite points of the intersection curve of the 3D surface model and the radial frontal plane in a portion representing the neck of the bone;

iii) computing an radial axial plane orthogonal to the radial frontal plane and passing through the adjusted neck axis adjusted in the radial frontal plane;

iv) adjusting the precise neck axis in the radial axial plane so that the adjusted neck axis passes through the middle of the minimal segment joining two opposite points of the intersection curve of the 3D surface model and the radial axial plane in a portion representing the neck of the bone.

Advantageously, the user is asked to validate the resulting precise neck axis and, in case of failure of the automatic determination of a valid precise neck axis, the determination of the precise neck axis is carried out manually by drawing a line in two orthogonal 2D slices selected in the 3D image of the bone.

Another object of the invention is a system for precise determination of the head center and radius and the neck axis of an articulated bone from acquired 3D medical images of an articulation, the articulation comprising two bones one of which is said bone with a head and a neck, the system comprising a computer including a memory and a processing unit adapted to run a computer program, wherein said computer program comprises at least one algorithm applying the method as described above.

DETAILED DESCRIPTION OF THE INVENTION

Figure 1:
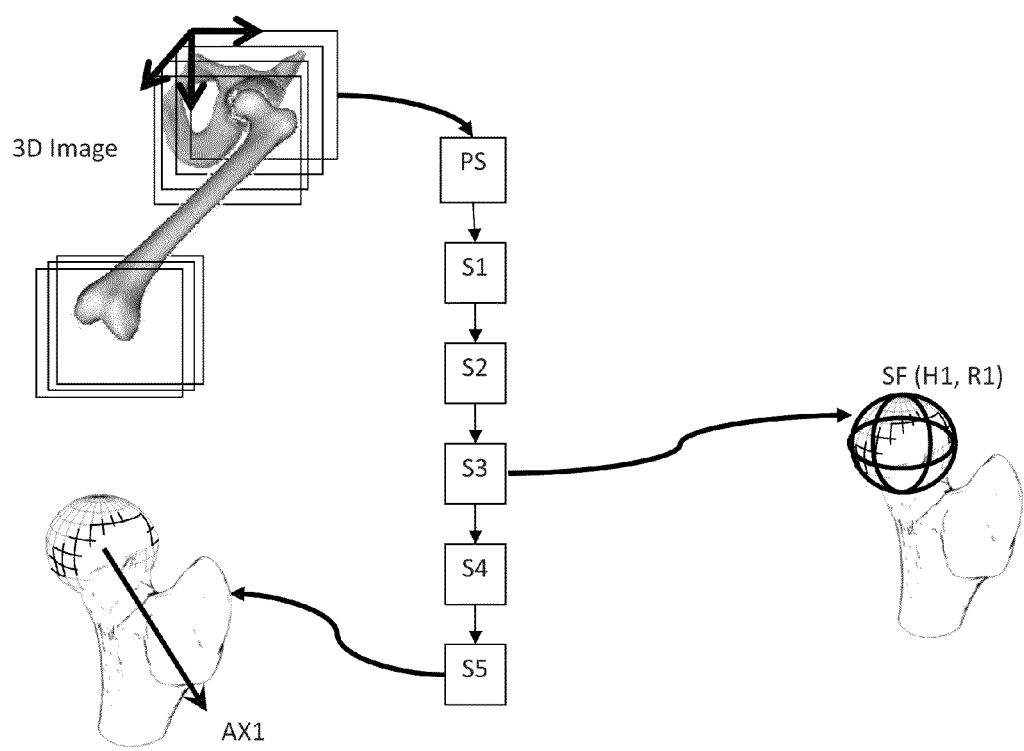
FIG. 1 is a representation of the different steps being performed in the method, illustrating the initial input, the final output and the intermediates steps.

Hereafter, description of the invention will be made with reference to the articulation of the hip. However, the invention is not limited to this illustrative example and the person skilled in the art will easily transpose this description to any other articulation partially formed by a bone head, such as the shoulder.

Some critical anatomical elements are necessary to measure some specific anatomical characteristics of the proximal femur, such as the femoral neck version and inclination angles, and a newly defined 3D measure of alpha angle, which participates in the characterization of the proximal femur deformity in Femoro Acetabular Impingement (FAI) pathology.

The method is specifically addressing the femur but it can be extended to other bones of the human or animal body such as the humerus or other bones having a rotoid articulation. The general purpose of the invention is to determine automatically from the 3D image the major characteristic geometric elements of an articulated bone that is constituted of a head and a neck in a fast, reproducible and precise manner. The head of the bone is assumed to have a spherical portion and the neck is assumed to have roughly a diabolo shape. A major difficulty is to define accurately the sphere that best represents the head and the axis that best represents the major neck direction. It is then also necessary to define additional geometric characteristic elements from those critical components, which is also a difficult task.

In standard practice, the determination of those characteristic elements of a bone are performed manually by the radiologist on the 3D image, using interactive software tools that rely mostly on reformatted 2D images in the 3D image volume. Working on 2D images for determination of 3D geometric elements leads to errors. Interactive software using a mouse is also prone to human errors. And in all cases, such determination is time consuming.

In order to compute accurate characteristic anatomical values for the femoral bone features such as neck version angle, neck inclination angle and the alpha angle in three dimensions, the computations need to be based on the precise determination of the following reference anatomical elements: the femoral head sphere center and radius, and the femoral neck axis. The purpose of the invention is to describe a method of automatic and accurate determination of those critical geometric elements from the 3D image, in order to compute precise characterization values of the femoral deformity very quickly.

A 3D computer tomography (CT) examination of the patient is performed in order to provide a 3D image of the hip bones using a specific predefined protocol. In addition to the conventional 3D image acquisition protocol for the hip, the method requires the acquisition of a few extra CT images at the level of the knee. The 3D image can be a stack of parallel 2D images, providing a volume of voxels, each voxel supporting a gray level value in the case of CT image. This step can be directly included in the method of the invention or carried out previously.

The method is implemented as image processing software running on a standard computer. The user can interact with the software by a standard user interface medium like a mouse, touch screen or the like. Images are displayed on the monitor of the computer. At the beginning, the software is used to select and load the 3D image of the specific patient.

As shown in FIG. 1, the method contains successive steps, using as input the 3D image of the bone, and producing as output a precise sphere SF fitting the head of the bone and defined by a precise head center point H1 and a precise radius R1, and an axis AX1 determining the neck axis direction and position of the bone.

Figure 2:
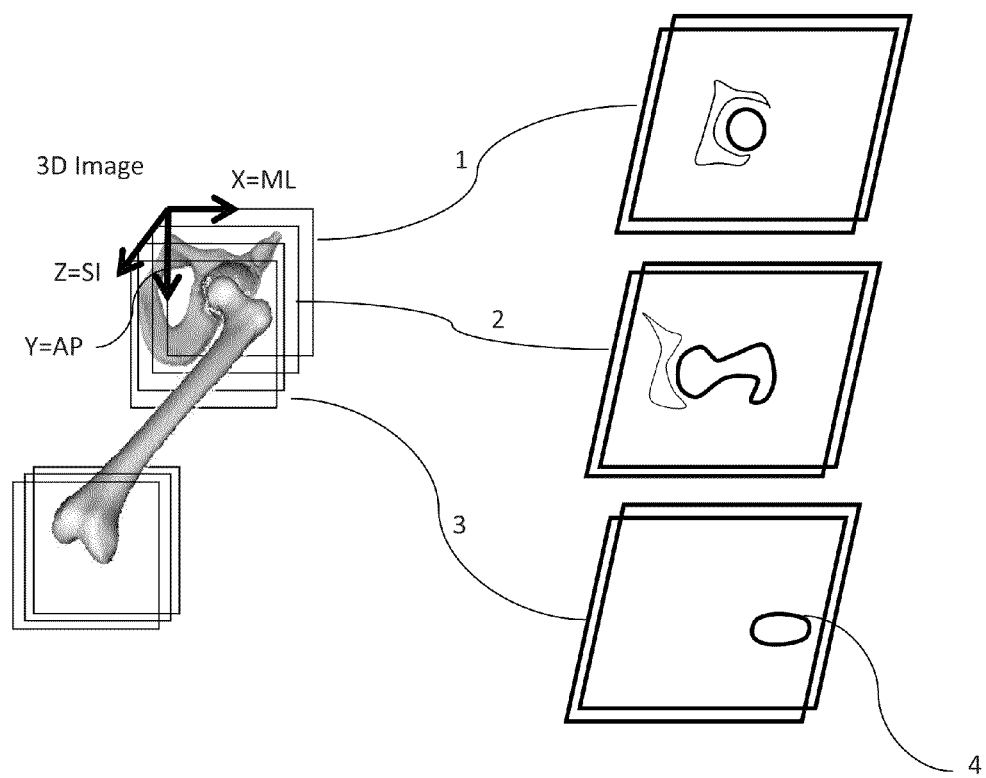
FIG. 2 is a representation of the extraction and identification of connected components belonging to the bone with a head and a neck in the 3D medical images slices.

An initialization is performed by orientating the 3D image relatively to anatomical orientation. In case of CT, the 3D image is generally composed by a series of axial slices, the patient laying on the back, feet first in the medical imaging device. From this a priori knowledge of the patient position and 3D image acquisition parameters, it is possible to determine automatically the anatomical orientation of the 3D image from the coordinates system of the 3D image. As shown in FIG. 2, in the case of a hip CT exam, the anatomical orientation is as follows: the X axis corresponds to the medio-lateral direction ML, the Y axis corresponds to the anterior-superior direction AP and the Z axis corresponds to the superior-inferior direction SI. Slices 1, 2 and 3 are examples of slices of the 3D image in planes perpendicular to the Z axis.

The preliminary step PS first consists in extracting from the 3D image connected components corresponding to the external surface of the bones and to label them with the different bone structures of the articulation they belong to. By "connected component" is meant a set of voxels having values within a predefined range and forming a chain so that the voxels of the set have at least one apex, one ridge or one face in common. The method to perform this is first, in the case of CT image, applying well known thresholding operator on the 3D image to select voxels which value is beyond a predefined threshold value. The threshold value generally represents a cortical bone level in Hounsfield units. It is also possible to define one high threshold value and one low threshold value and selecting voxels which value is in the range defined by the two threshold values. This first operation generates multiples connected objects in the volume of the 3D image. Additional processing using well known mathematical morphology operators are applied to those binary objects to eliminate small connected components and to fill the inside of closed surfaces so that only the voxels of the external surface of the bone are selected.

Figure 3:
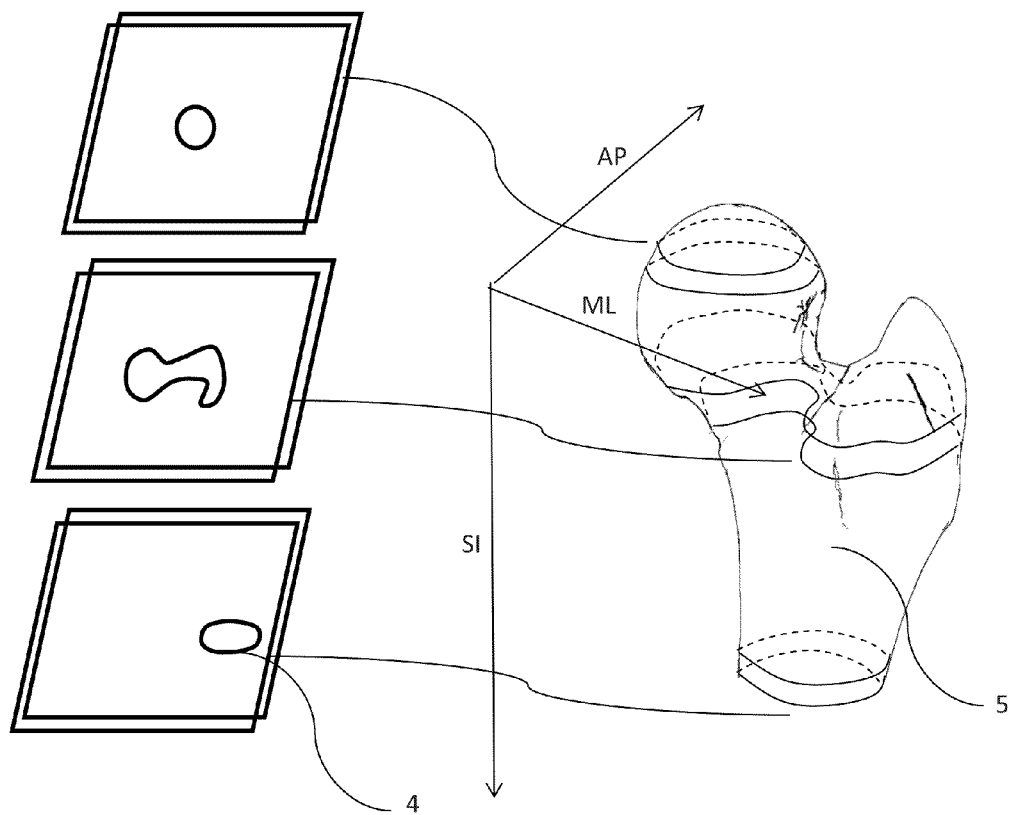
FIG. 3 is a representation of the construction of a 3D connected component labelled as the bone with a head and a neck.

Secondly, in order to label the connected components with the bone structure they belong to, the method consists in searching automatically in the most inferior slice 3 of the 3D image the largest closed 2D connected component 4, as belonging to the distal shaft of the bone with a head and a neck. As shown in FIG. 3, from that initial operation, the labelling of the connected component 4 is then propagated in the superior direction to the successive slices, thus determining a 3D connected component; defined as a 3D contour 5 of the bone with a head and a neck.

Figure 4:
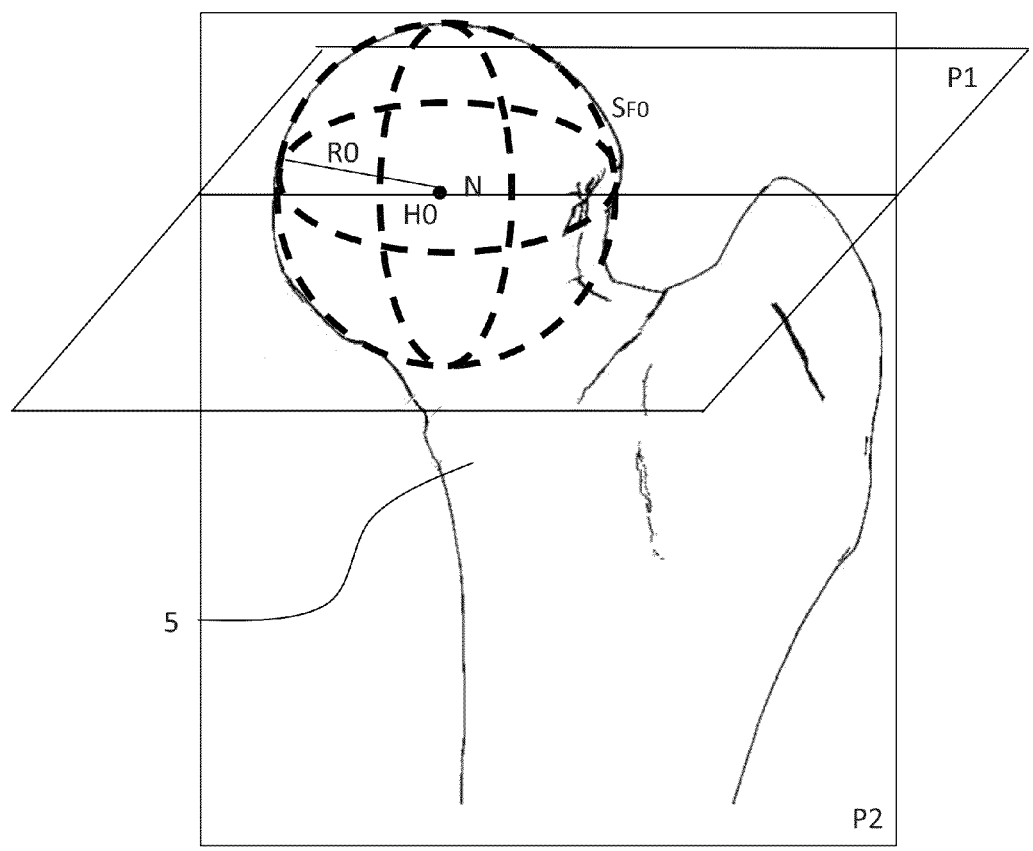
FIG. 4 shows a general silhouette of the proximal femur showing 3D connected component contours, with a sphere approximation on the femoral head and an approximation of the neck axis.

As illustrated in FIG. 4, the first step S1 of the method is intended to determine automatically in the space of the 3D image an approximate sphere SF0 fitting to the head portion of the bone with a head and neck, by locating an approximate 3D sphere center point H0 and defining an approximate radius R0. In a preferred embodiment of the same step S1, the femoral head sphere SF0 with center H0 can be automatically detected using the method described below.

Figure 5:
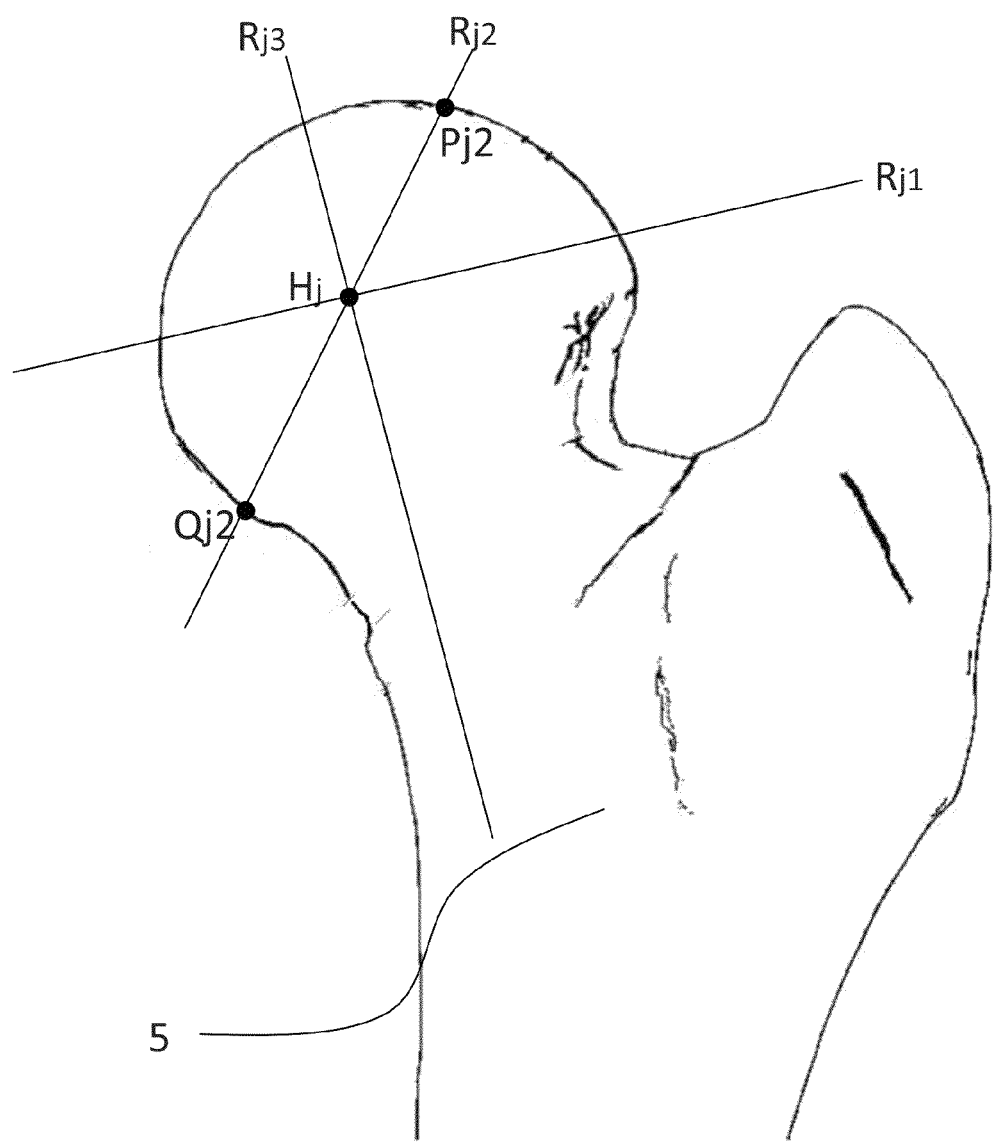
FIG. 5 is a general cross-sectional view of the proximal femur showing the intersection of the 3D connected component contours with lines passing through a candidate point of the head center.

Each point Hj (j being an integer greater than 1) of the inside part of the volume delineated by the 3D contour 5 is a candidate for being the femoral head center H0. A regular three dimensional grid of those inside points Hj is built with spacing of, for example, one millimeter between two points of the grid. For each point Hj, a spherical score is computed in the following way. As shown in FIG. 5, a predefined and constant number M (M being an integer greater than 1, and possibly in the range of 360×180 in order to cover a full 3D sphere at regular intervals of 1° solid angles) of rays Rji (i being an integer comprised between 1 and M) are drawn from the candidate point Hj. For each rays Rji, points Pji and Qji are computed as the intersection of the ray Rji with the 3D contour 5. This pair of points (Pji, Qji) is recorded together with an assumed radius value rji which is half of the distance between Pji and Qji. The radius values rji are sorted and accumulated in joint intervals [Rk−ϵ; Rk+ϵ] where ϵ defines the half-width of the intervals, and where Rk is an average value of the radius values rji belonging to this interval. The interval [Rk−ϵ; Rk+ϵ] having the maximum number MAXj of cumulated radius rji is computed and the value MAXj is stored. The interval width E is typically ranging from 1 to 2 mm. The ratio MAXj/M indicates the likelihood of the candidate point Hj to be the head center. Indeed, if the point Hj is the center of a perfect sphere, it will have a ratio of 1 which is the maximum. This ratio MAXj/M is named the spherical score. The search process is applied to all points inside the 3D contour 5 on a regular volumetric grid every 1 mm to find the point H0 with the greatest spherical score.

In practice, many optimization methods can be applied to avoid searching the solutions among all points inside the surface on a regular grid in order to speed up the search. For instance, the radius of a femoral head is known a priori to be within 15 and 40 mm, and the rays can be first drawn on the 6 anatomical direction (AP, ML, SI), so that if the points hit by those rays have a distance which does not fall in the range (15 mm,40 mm) with respect to the candidate point Hj, the candidate Hj is eliminated right away so that the spherical score does not need to be calculated.

In another embodiment of the same step S1 for the estimation of the head center H0, a 4D Hough transform is applied to the points of the 3D surface model. The equation of the searched sphere is $(X-X0)^2+(Y-Y0)^2+(Z-Z0)^2=R0^2$ where (X0,Y0,Z0) are the coordinates of the sphere center and R0 is the radius of the sphere. A point that is lying on the 3D contour 5 (Xm,Ym,Zm) generates a surface in the 4 dimensional parametric space (X0,Y0,Z0,R0) defined by its equation $(Xm-X0)^2+(Ym-Y0)^2+(Zm-Z0)^2=R0^2$. Each surface point (Xm,Ym,Zm) generates a sphere in the Hough space (X0,Y0,Z0,R0). Points drawn by those spheres are accumulated. When all surface points of the 3D surface model have been processed, the point in the 4D Hough space (X0,Y0,Z0,R0) having the maximal number of accumulated points is selected and it defines estimation of the head center H0=(X0,Y0,Z0). In practice, the search space is a Hough space bounded in the R dimension to [15 mm, 40 mm] interval and in the X0,Y0,Z0 dimensions are bounded by the values that define a bounding box around the 3D contour 5, and it is possible to use an interval of 1 mm in the R dimension so that we have only 25 points in this dimension, and we can use an interval of 3 mm for the X0,Y0,Z0 dimensions for a range of about 90 mm, which means 30 values for each of those axis. In total it means a Hough space with 25×30×30×30 intervals in which the surface points are accumulated.

Figure 6:
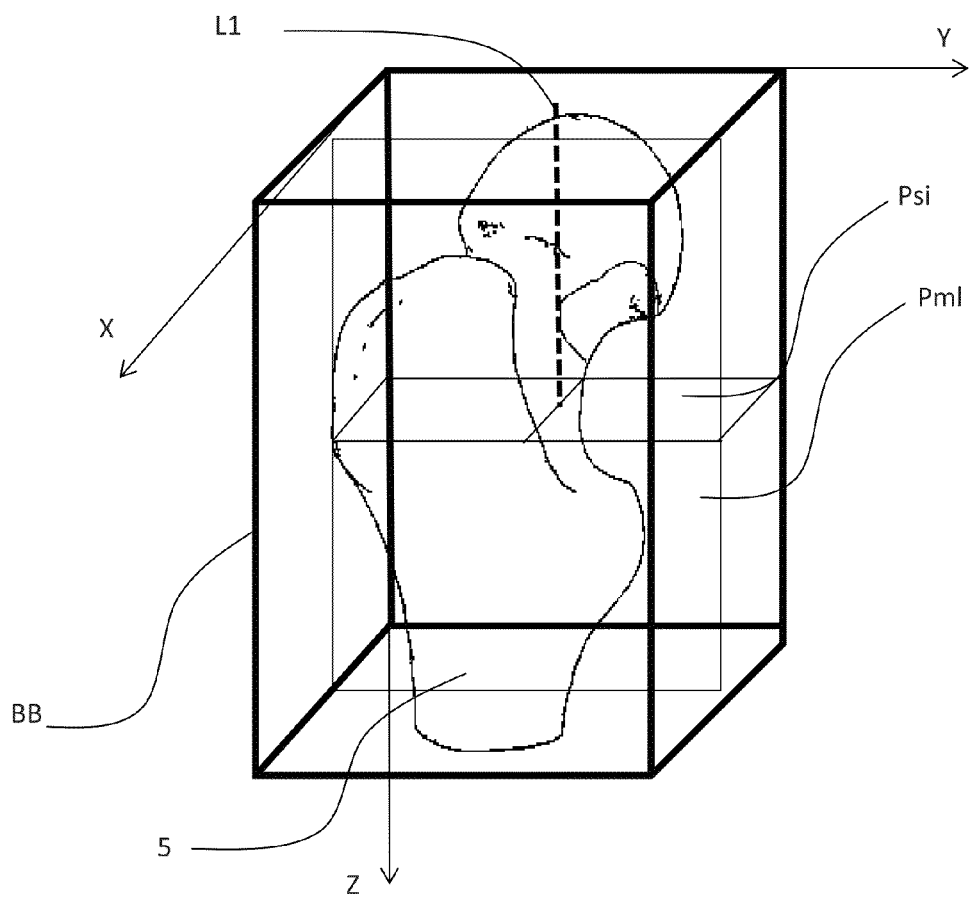
FIG. 6 is a perspective view of the 3D connected component of the femur showing a bounding box and its subdivisions to reduce the search for head center point candidates.

In one embodiment of the method, an optimization of this step S1 is also to reduce the volume of search for the location of the point H0. As shown in FIG. 6, a bounding box BB can be determined as being the smallest rectangular box containing the 3D contour 5. From a priori knowledge of the anatomy and position of the bone defined by the 3D contour 5, the bounding box BB can first be split in two halves by a plane Pml orthogonal to the X medio-lateral direction and passing through the middle of the bounding box BB. Then only the most medial half is considered, and is also split in two by a plane Psi orthogonal to the Z superior-inferior direction passing through the middle of the bounding box BB, only the most superior part being then considered, the considered volume being know reduced to one fourth of the initial bounding box BB volume. Now the search methods described above for the determination of the point H0 can be applied only along the short segment L1 being a vertical segment in the Z superior-inferior direction passing through the middle of the considered fourth of the bounding box BB.

In another preferred embodiment, the user can validate the approximate sphere resulting from one of the automatic computation described previously from a display of the resulting approximate sphere overlaying the 3D image of the bone. There can be cases where the automatic computation of the approximate sphere fails, for various reasons such as a bad image quality or the presence of artifacts which can create for example holes or unwanted extensions in the 3D connected component of the bone. In case of failure of a valid approximate sphere determination, the user can manually determine in the 3D image the approximate sphere as follows: the user chooses among the axial slices of the 3D image a plane P1 in which the head center is best visible and may be located. Then the user selects with the user interface medium a point N of this plane P1, which defines a plane P2 orthogonal to plane P1 that comprises the selected point N. The intersection of the planes P1 and P2 with the 3D image allows the user to identifying the center H0 of the femoral head in both planes. An interactive adjustment of the radius R0 of a circle centered on H0 in each image is also proposed to roughly fit with the head contours.

The next step S2 of the method consists in creating a 3D surface model from the 3D contour 5 defined above. In the case when the 3D contour 5 defines for sure only the bone with the head and neck, this step consists in just applying well known conventional marching cube or divide cube methods or similar in order to produce the 3D surface model from the 3D contour 5.

However, the 3D contour 5 may be a merge of the contours of the bone with the head and a neck and of contours of adjacent bones and hence create some defects such that the 3D contour 5 also contains connecting component which do not belong to the bone with the head and neck. Those imperfections are due to many phenomena including the quality of image acquisition and reconstruction, but also to the poor quality of bone density in some pathological areas. Such cases can be automatically detected by comparing the bounding box BB of the 3D contour 5 to expected approximate bounding box size from a priori knowledge of the anatomy. In these cases, it is necessary to force the elimination of the extra connected components not belonging to the bone with a head and a neck.

Figure 7:
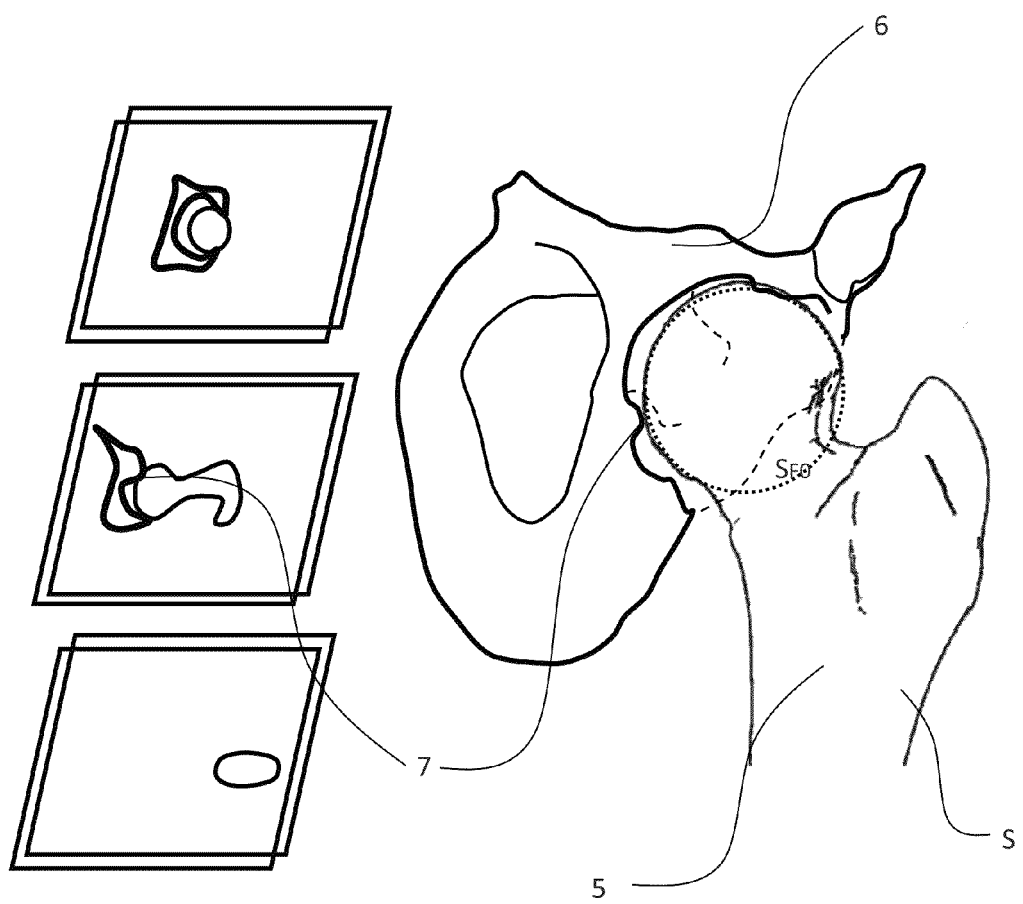
FIG. 7 illustrates the case when the 3D connected component of the femur is merged with the socket bone of the pelvis, and for which the approximate fitted sphere is used to force the separation between the two bones components.

Usually, as shown in FIG. 7, for 3D image of an articulation, this merge of the bone components take place in region of the head 7, and the 3D contours 5 are merged with the 3D contours 6 of the socket of the other articulation bone, creating a very large 3D connected component. When such cases are detected, the proposed method comprises a process to force the separation of 3D contours 5 and 6 before generating the 3D surface model. The process uses the contour of the approximate sphere SF0 to determine the limit between the two bones, and cuts the large 3D contour at the merging locations two create two separated 3D contours 5 and 6. In cases where the forced separation generates discontinuity holes within the 3D contour 5, the surface defined by the approximate sphere SF0 is used to fill up these holes and regenerate a complete 3D contour of the bone.

The known conventional methods mentioned above are then used on the isolated 3D contour 5 in order to create a 3D surface model S of the bone with a head and neck.

Figure 8:
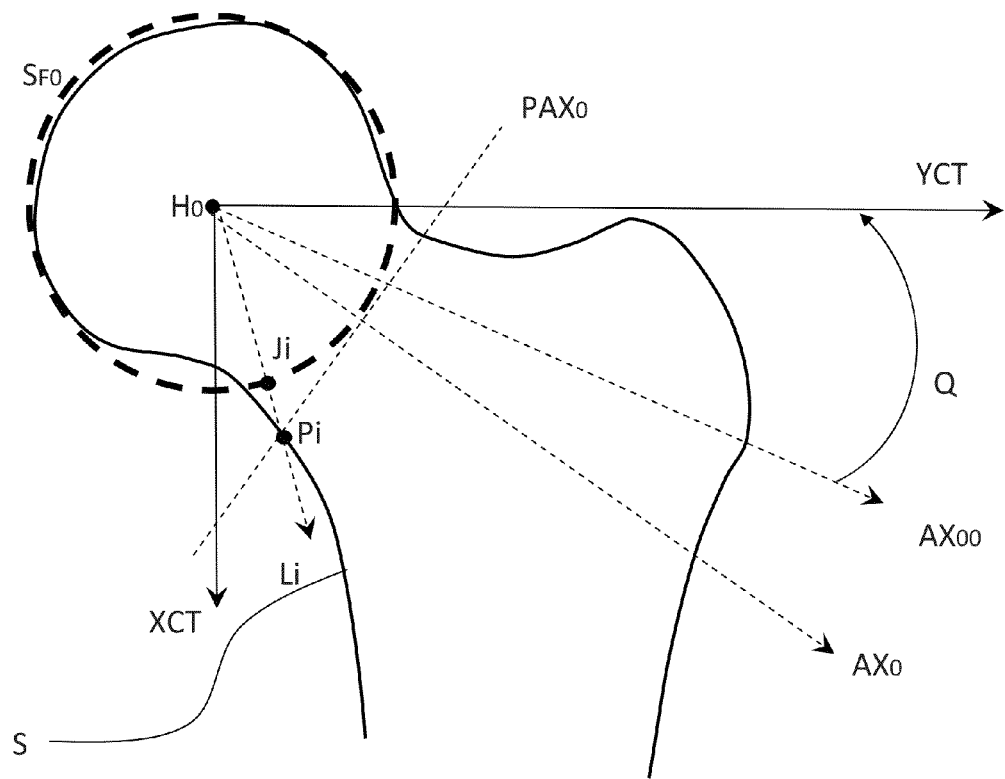
FIG. 8 is a general cross-section view of the femur showing the approximated sphere fitted to the femur head and a quadrant section within to search for the initial approximated neck axis.

The next step S3 of the method aims at the determination of an approximate neck axis in the constructed 3D surface model. In a preferred embodiment, as represented in FIG. 8, using the approximate head center H0 and radius R0, an estimation of the neck axis represented by an axis AX0 can be computed. A predefined number of N hemi-lines Li, for an index i varying from 1 to N (N being an integer greater than 1), and emerging from the point H0 are drawn in 3 dimensions. Since bone orientation is usually known approximately with respect to the 3D image coordinate system (Xct, Yct, Zct), a rough initial estimation of the neck axis is known, it can be for instance a first estimation axis AX00 that passes through H0 and that makes an angle Q with the Yct axis and that is in the plane defined by H0, Xct and Yct. The angle Q can be 30° for example. The hemi-lines Li constitute a bundle of lines starting from H0 and extending within a cone around the first estimation axis AX00, the cone having a very large aperture angle of 80° for example. This step avoids drawing hemi-lines Li in a direction opposite to the real value of the neck axis AX0 in which some outliers could be found. The number N of hemi-lines Li can be for instance 360×80 in order to spread around the estimation axis AX00 every degree, but it can be also a subsample that is used such as 90×20=1800 lines in order to search every 4 degrees, which is the preferred embodiment.

For a given hemi-line Li, the point Ji of the hemi-line Li that intersects the sphere SF0 is calculated and the point Pi of the hemi-line Li that intersects the bone surface model S is also calculated. Methods for computing the intersection of a line with surfaces and spheres in 3 dimensions are well known in the art. The distance (H0Pi) between the head center H0 and the point Pi and the distance (H0Ji) between the head center H0 and the point Ji are computed and then compared. If the distance (H0Pi) between H0 and Pi is superior to the distance (H0Ji) between H0 and Ji and if the difference (H0Ji)−(H0Pi) is below an arbitrary threshold value η such as 2 mm for example, the point Pi is stored in the memory of the computer, that is if:

$$(H0Pi)>(H0Ji) \text{ and } (H0Ji)-(H0Pi)<\eta. \qquad [A]$$

The 3D curve made of the points Pi defines the edge of the head sphere on the 3D surface model. It is named the edge 3D curve. Then least-square fitting plane PAX0 is calculated from all the points Pi that have been stored using conventional robust methods for the estimation of a plane from a cloud of points, including automated elimination of outliers. The line which is orthogonal to the plane PAX0 and passing through H0 is the estimated axis AX0.

In another preferred embodiment of step S4, an estimation of the neck axis represented by an axis AX0 can be computed using the following method. Like in the previous methods, series of hemi-lines Li are drawn from the point H0 around the axis AX00. For each line Li, 180 planes Pij passing through Li are computed for an index value j varying from 1 to 180 every degree. For each plane Pij the maximal distance Dij between the hemi-line Li and the curve defined as the intersection of the plane Pij and the bone 3D surface model S is computed in a small region located at a known distance from the point H0 in order to avoid the regions where Li intersects the surface model S. The distance between two objects, lines, surfaces or curves, is defined as the minimal distance between the respective points of each object. For a given hemi-line Li, the smallest value Di amongst the values Dij is determined and stored. The hemi-line Li having the smallest value Di is considered as the axis AX0.

In another preferred embodiment, the user can validate the approximate neck axis resulting from one of the automatic computation described previously from a display of the resulting approximate neck axis overlaying the 3D image of the bone. There can be cases where the automatic computation of the approximate sphere fails, for various reasons such as deformed neck pathologies. In case of failure of a valid approximate neck axis determination, the user can manually determine in the 3D image the approximate neck axis as follows: the user chooses among the axial slices of the 3D image a first plane in which the neck is best visible and may be located. Then the user draws with the user interface medium a line in this first plane defining the main direction of the neck. Then a second plane orthogonal to the first plane that comprises the drawn line is displayed. The user can then adjust the orientation of the line in the second plane, the line defined in both the first and second plane determining the approximate neck axis.

The last two steps of the method consist in refining the determination of previous approximate geometrical elements.

Figure 9:
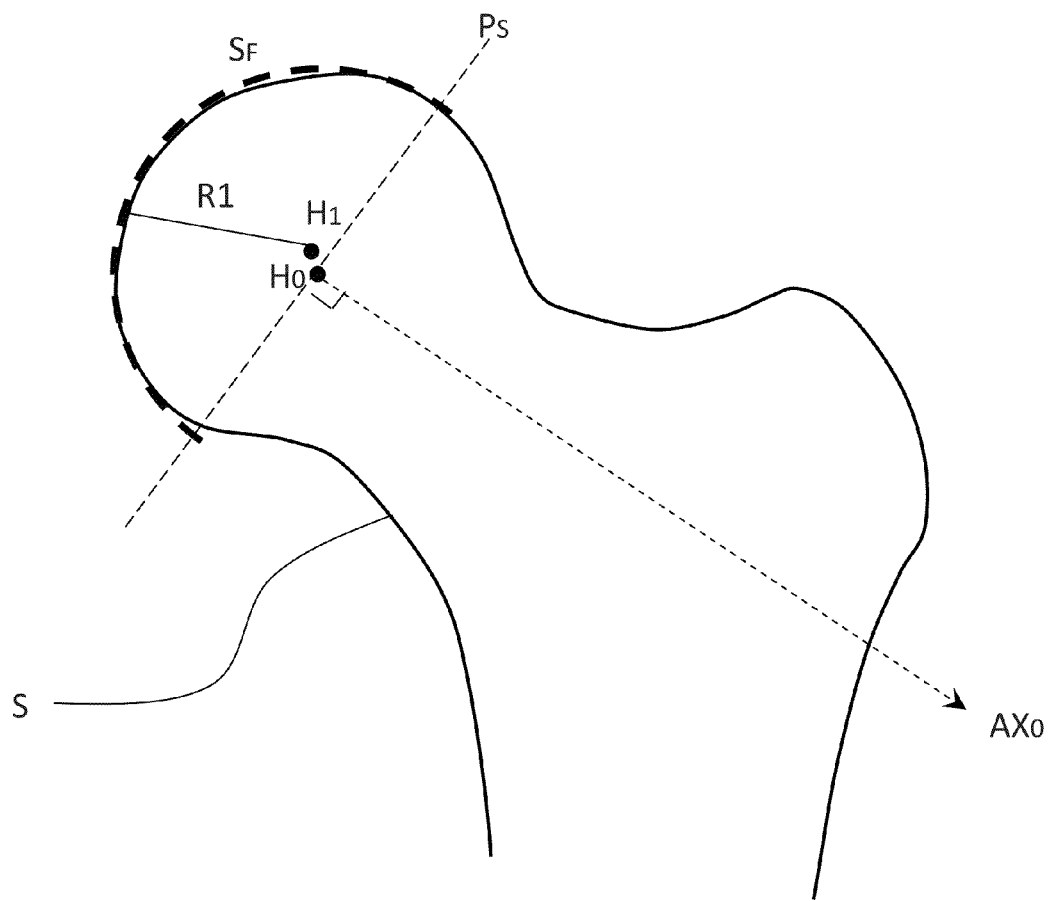
FIG. 9 is a general cross-sectional view of the proximal femur showing approximate femur head center and approximate neck axis, as well as the hemi-sphere fitting the spherical portion of the head.

First in step S4, a precise adjustment of the head center and radius is computed. As shown in FIG. 9, multiple rays are drawn from the initial center H0 until they intersect the external surface of the 3D bone model S. Only the half sphere opposite to the femoral axis AX0 is considered, that is the half sphere cut by a plane PS orthogonal to the neck axis AX0 and passing by the initial point H0. The cloud of points detected on the femoral head surface is fitted to a sphere using a conventional robust least squares technique including elimination of outliers. It provides a new head center H' with a radius R'. The algorithm is repeated with a new initialization by that new head center. In the least squares process, a conventional robust method is used. Points having a distance superior to N times the variance of the residual distances (noise) are eliminated as outliers. N is an arbitrary value that is typically 2 or 3. After elimination of outliers, the algorithm is repeated. The final result is the precise sphere SF fitting the normal area of the femoral head, from which the head center H1 and radius R1 are determined.

In another preferred embodiment, the user can validate the precise sphere resulting from one of the automatic computation described previously from a display of the resulting precise sphere overlaying the 3D image of the bone. In case of failure of a valid precise sphere determination, the user can manually determine in the 3D image the precise sphere as described previously for the determination of the approximate sphere.

Figure 10:
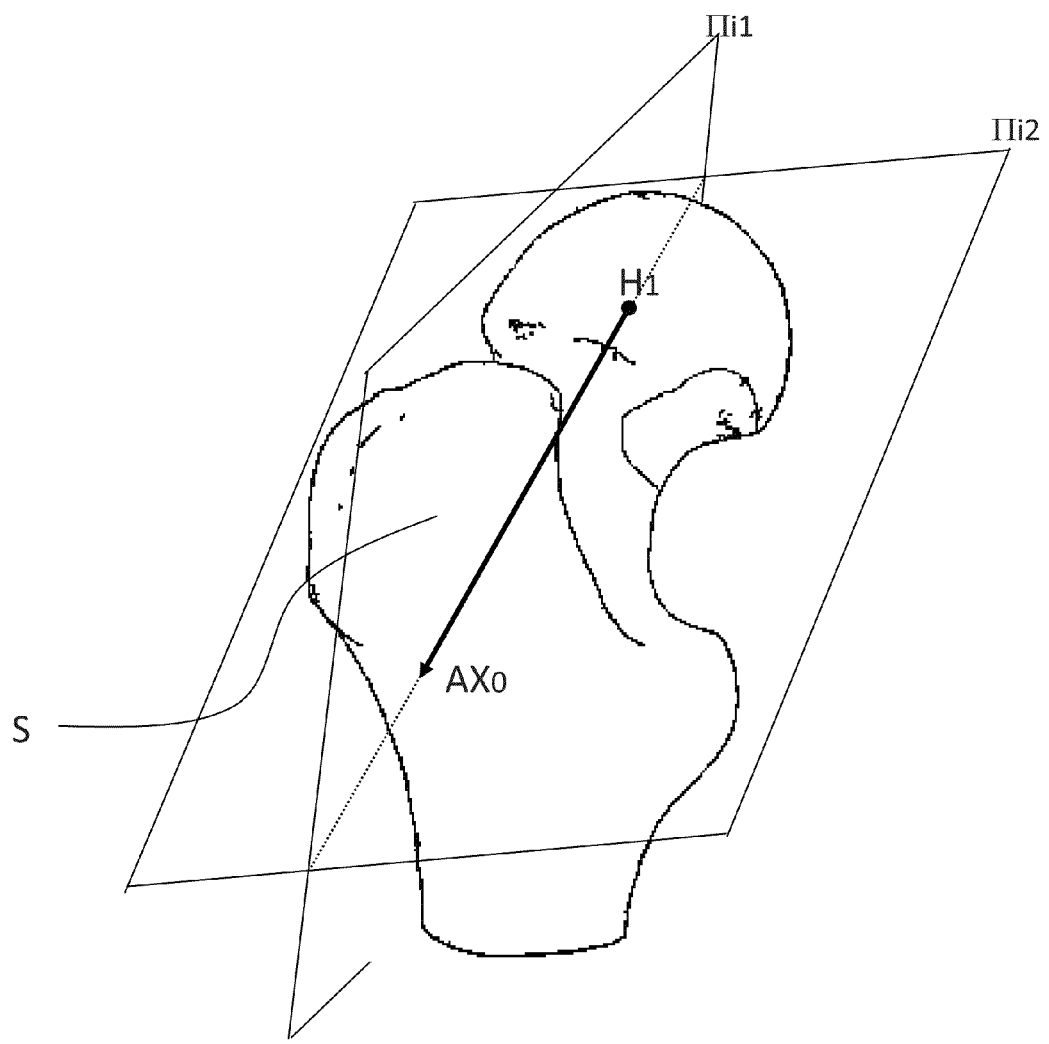
FIG. 10 is a perspective view of the proximal femur, showing different radial planes along the approximate neck axis.
Figure 11A:
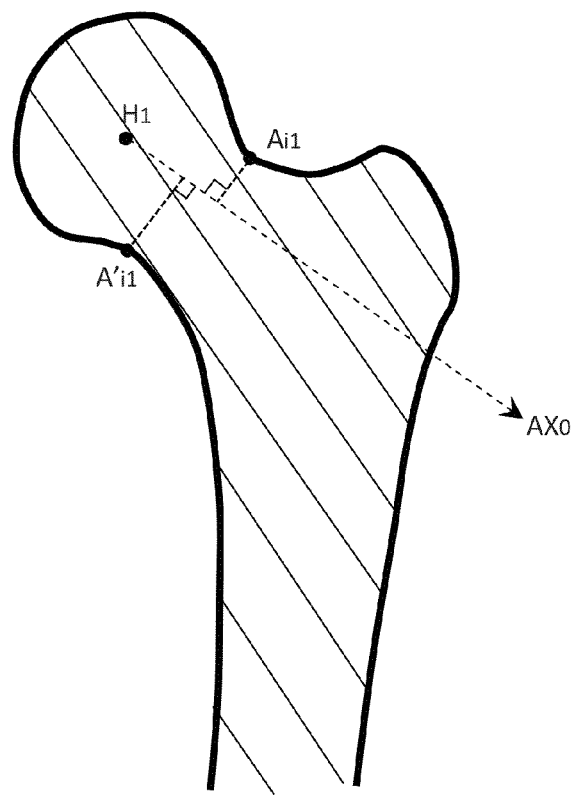
FIGS. 11A and 11B show cross-sectional views of the proximal femur computed from two radial planes along the initial neck axis, the two planes being orthogonal to one another, and showing the neck surface points closest to the approximate neck axis.
Figure 11B:
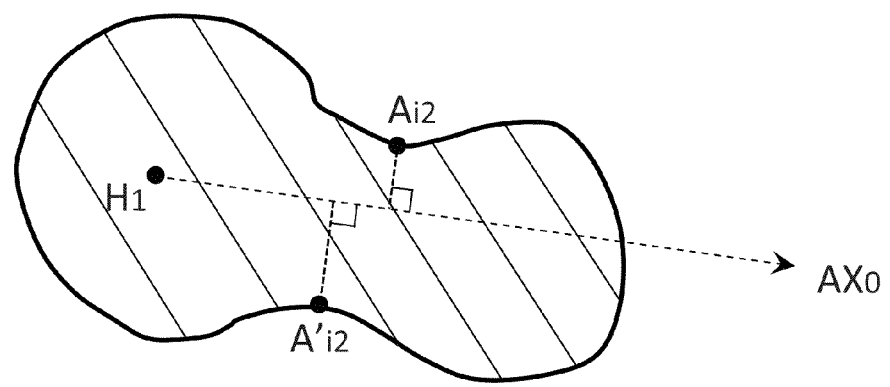

Then in step S5, once both the head center point H1 and radius R1 have been adjusted precisely, the neck axis AX0 is adjusted precisely. In a preferred embodiment, for each plane $\Pi i$ passing through the neck axis AX0 and defined by an angle i varying from 0° to 180°, the two surface points Ai and A'i that belong to the surface S and, which are the closest to the initial axis AX0 are detected, one point on each side of the axis inside the plane $\Pi i$. As an example, two planes $\Pi i1$ and $\Pi i2$ are shown on FIG. 10 and the sections of the 3D surface model corresponding to those planes are shown respectively in FIGS. 11A and 11B including for each section a representation of the points Ai and A'i.

Figure 12:
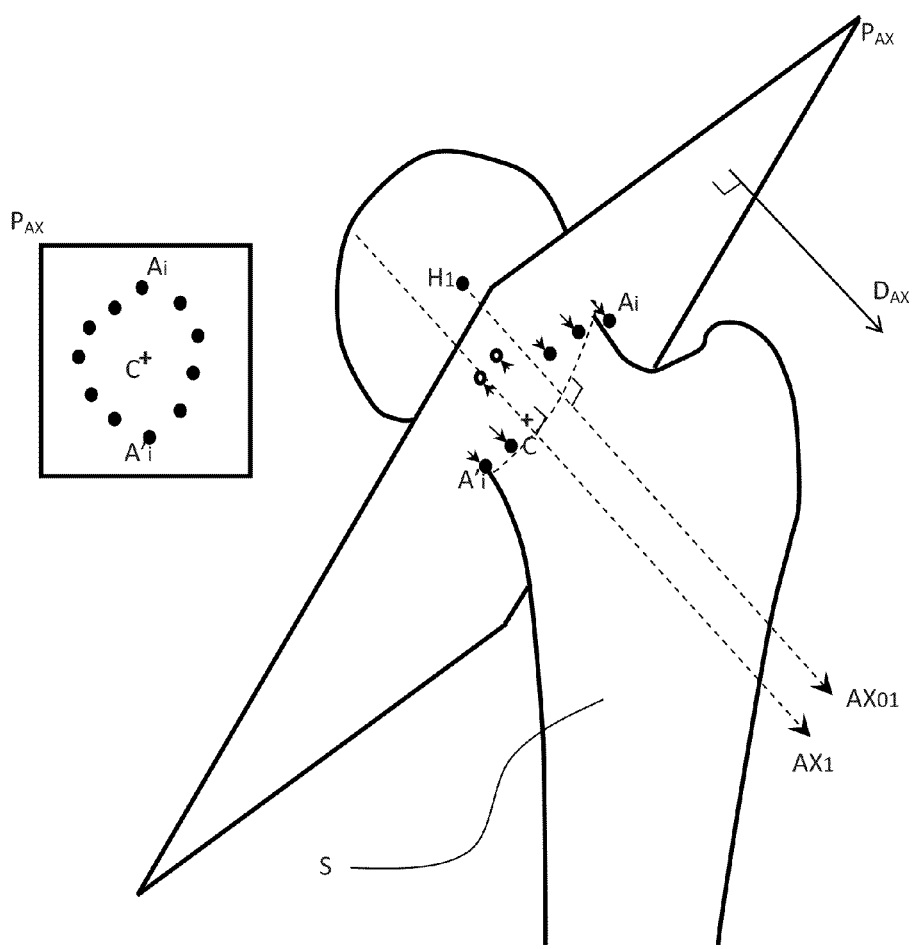
FIG. 12 is a perspective view of the femur showing the neck surface points closest to the approximate neck axis, with a zoom showing the projection these points on an average fitting plane.

As shown in FIG. 12, the collection of points Ai and A'i obtained by this method constitutes a 3D curve on the neck surface, roughly orthogonal to the initial neck axis. It is named the 3D neck minimal curve. A least-squares fitting to a plane is applied to the 3D neck minimal curve, resulting in the average plane PAX.

The orthogonal line to this plane PAX is the new neck axis direction DAX. At this stage, it is possible to define the new femoral neck axis AX01 by the femoral head center point H1 and the direction DAX. However, in some cases, the neck axis does not pass exactly through the femoral head center. To address this issue in the method according to the invention, the centroid of the 3D neck minimal curve is projected onto the plane PAX in a point C. The adjusted femoral neck AX1 is thus determined by the point C and the DAX direction. Concerning the least-squares fitting step, outliers are eliminated using conventional methods. The process of computing the Ai and A'i pairs of points to determine the neck axis direction DAX and the point C is repeated until it converges towards a stable solution. The final result is the precisely adjusted position AX1 of the femoral neck axis.

Figure 13:
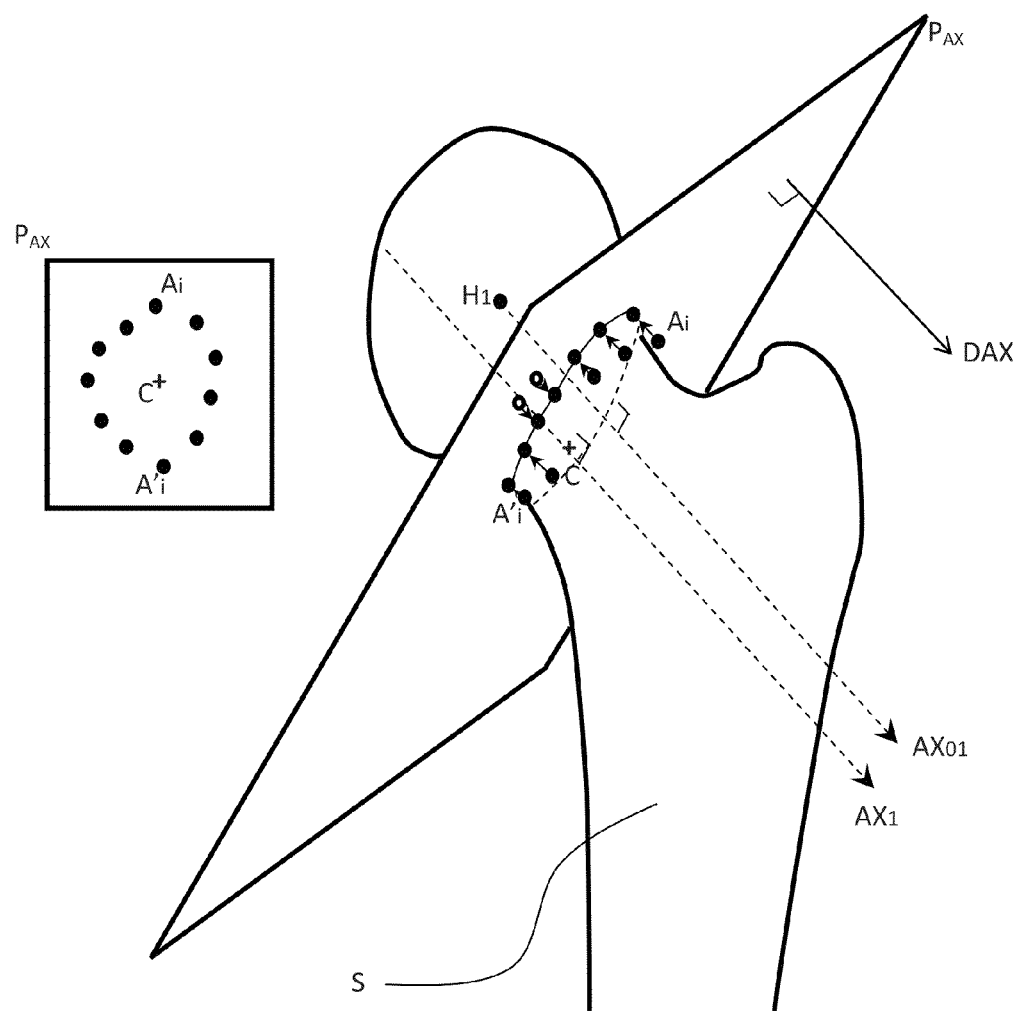
FIG. 13 is a perspective view of the femur showing the minimum 3D neck curve, with a zoom showing the projection of the points of the curve on an average fitting plane.

In another preferred embodiment for step S5, once the pairs of (Ai, A'i) points have been detected using the method described above, the method consists in minimizing an energy function of the sum of all contiguous (Ai,Ai+1) segments, as illustrated in FIG. 13. The method is searching to minimize the total length of the 3D neck minimal curve (A1,A2)+(A2,A3)+(A3,A4)+ . . . +(A'1,A'2)+(A'2,A'3)+ . . . with the constraint that the points A1, A2, . . . A'1, A'2, etc. . . . remain on the surface S. This is achieved by iterative methods similar to the well known snakes methods used in image processing. An analogy of the snakes methods would be to place an elastic rubber band around the neck and let it find equilibrium. This computation will converge to a new set of points Ai, A'i that constitute another method for calculating the 3D neck minimal curve. Then the rest of the method defined above is applied by computing a least squares fitting plane PAX to those new points Ai, A'i and the normal direction DX to that plane, and also the central point C, so that the precisely adjusted neck axis AX01 or AX1 are defined, AX01 for a definition passing through H1 and AX1 for a definition not passing through H1.

Figure 14A:
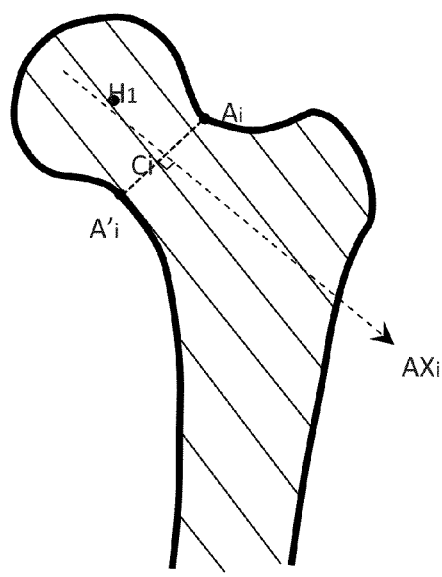
FIGS. 14A and 14B show cross-sectional views of the proximal femur illustrating the computation of neck center points as middle of neck shortest segments.
Figure 14B:
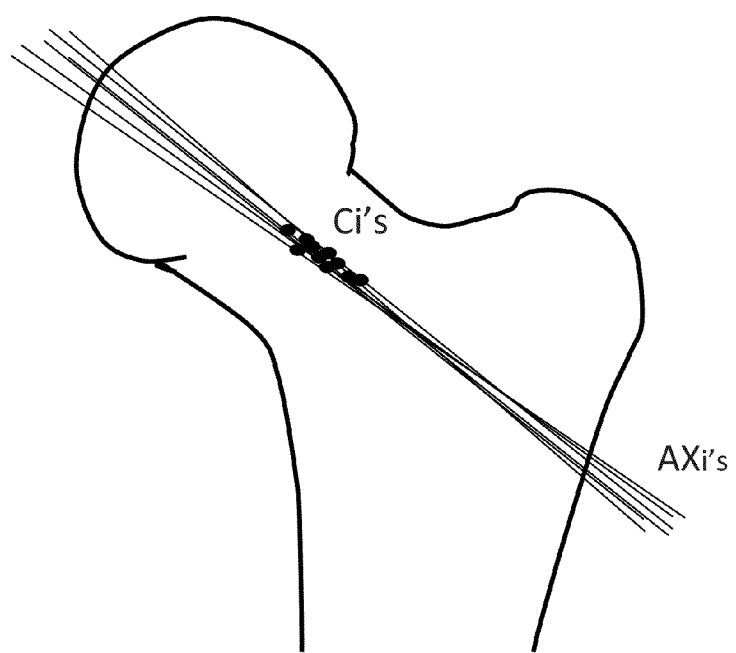

In another preferred embodiment for step S5, as shown in FIGS. 14A and 14B, for each radial plane Pi passing through the initial neck axis AX0, the two bone surface points Ai and A'i which define the shortest segment of the neck portion are detected. Ai and A'i lie on an opposite side of the surface with respect to each other. A neck axis AXi is then determined as orthogonal to the AiA'i segment, and passing by the middle of that segment Ci (see FIG. 14A). The precisely adjusted neck axis AX1 is defined as an average axis of all AXi axis (shown in FIG. 14B): the direction of the axis is the average direction of the AXi and the neck axis passes through the centroid C of all the Ci points.

Figure 15A:
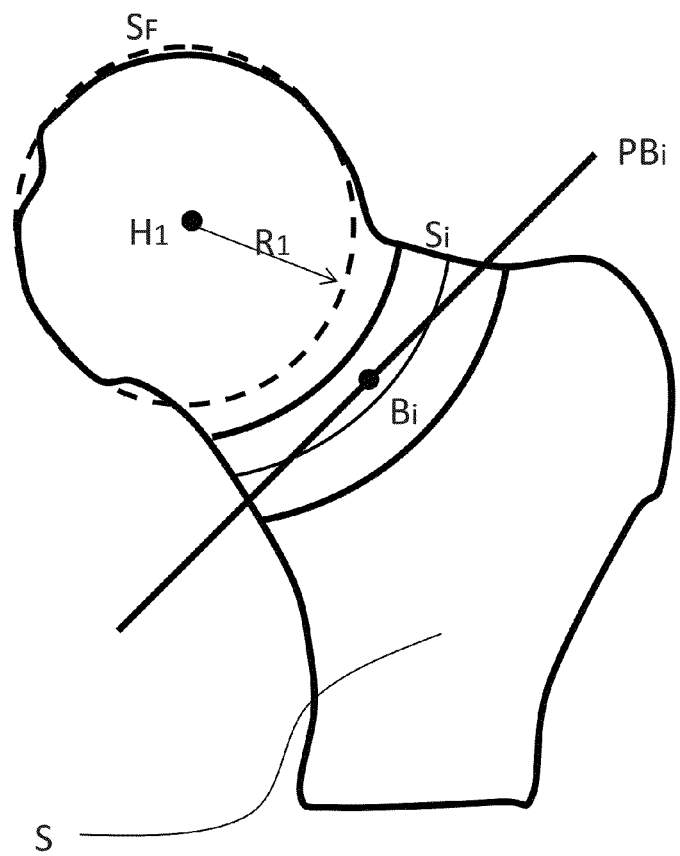
FIG. 15A is a general cross-sectional view of the proximal femur illustrating the computation of the intersection of growing sphere from the first approximate femoral head sphere and FIG. 15B is a cross-section view of the proximal femur in a plane passing through the barycentre of the intersection of the sphere with the 3D surface model.
Figure 15B:
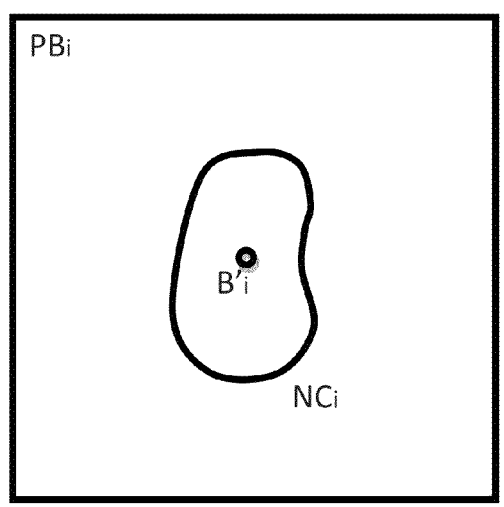
Figure 16:
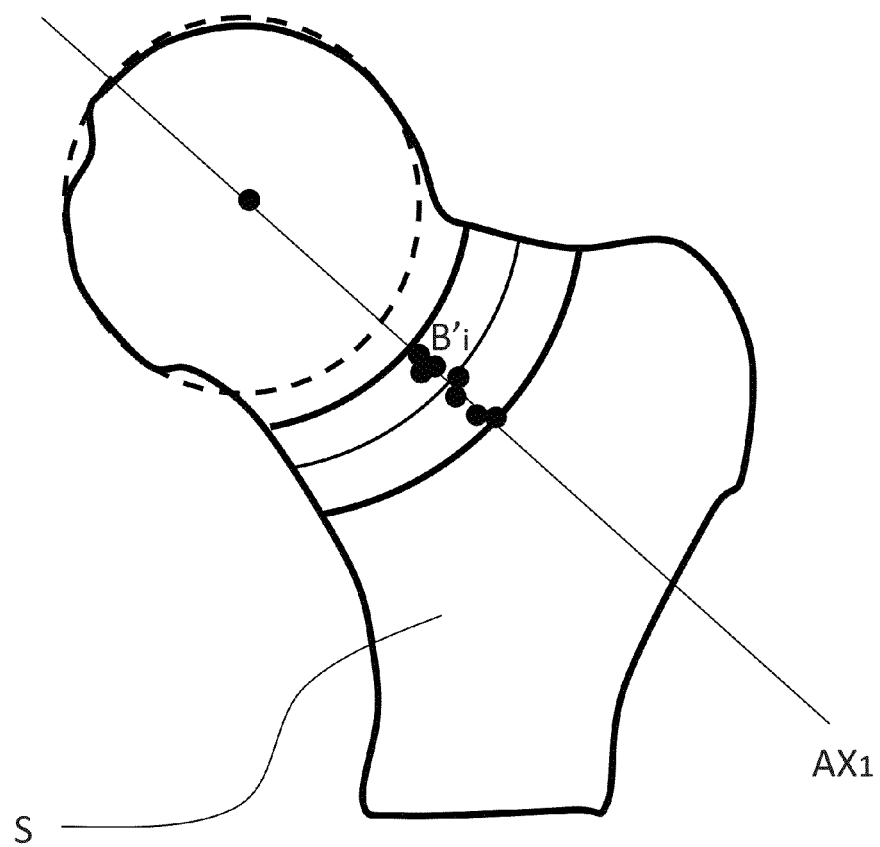
FIG. 16 is a general cross-sectional view of the proximal femur illustrating the computation of an average neck axis from the barycentre of intersection curves of growing spheres with the 3D surface model.

In another preferred embodiment for step S5, as shown in FIGS. 15A and 15B, for cases where it is most interesting to define the neck axis as passing through the head center H1, the following process is performed. A set of predefined number of N spheres Si is generated (N being an integer greater than 1, I being an integer comprised between 1 and N), starting with the precise sphere SF (H1, R1), and with growing radius, while centered on H1. The maximum radius is predefined so as to cover the neck portion of the bone to two times R1 for example. For each sphere Si, the barycentre Bi of the intersection of the sphere Si with the 3D surface model is computed. Then for each barycentre Bi, a plane PBi is determined as being orthogonal to the axis defined by H1 and Bi, and passing through Bi. Now each plane PBi intersects the 3D surface model determining a neck curve NCi. The new barycentre B'i of the neck curve NCi is then computed (see FIG. 15B). Finally, as shown in FIG. 16, the least-square fitting line passing through the set of points B'i and the point H1 determines a precise neck axis AX1 passing through the head center H1.

Figure 17:
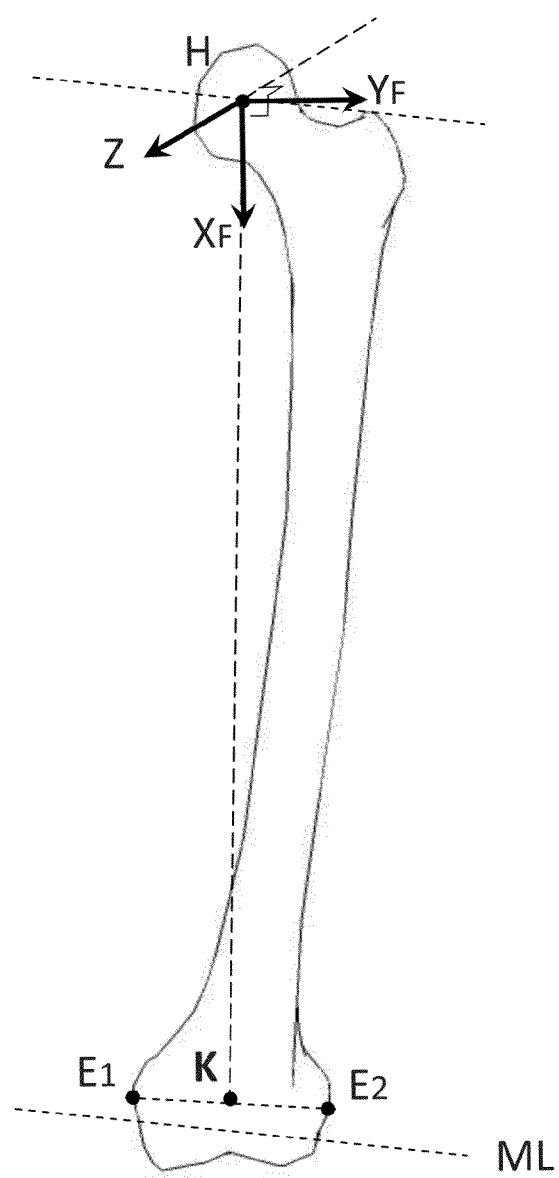
FIG. 17 is a global view of the femur illustrating the construction of the femur mechanical 3D coordinate system.
Figure 18:
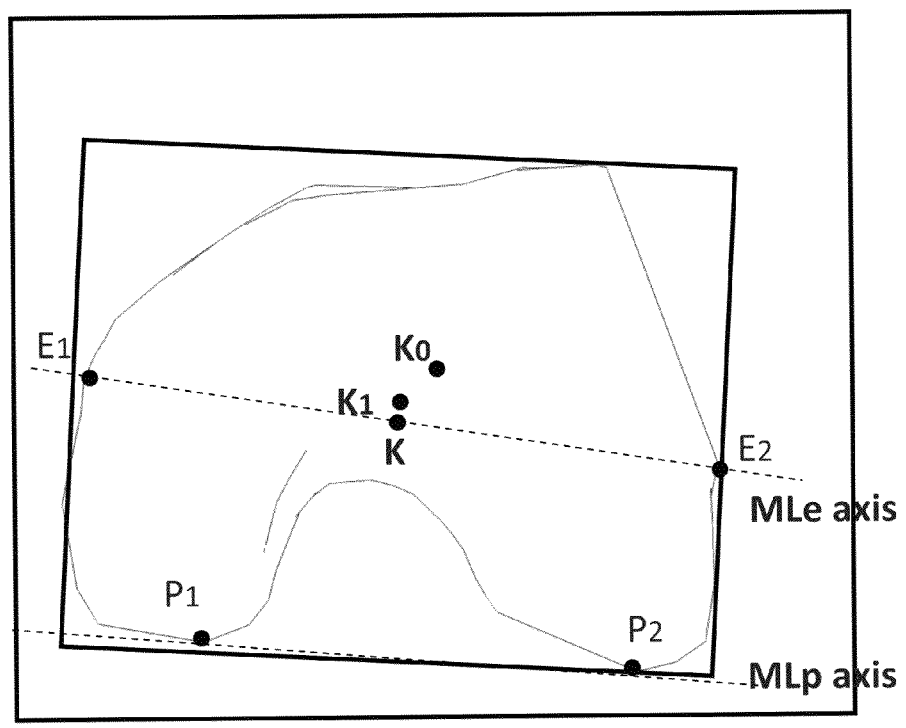
FIG. 18 is a cross-sectional view of the distal femur at the level of the knee, illustrating the computation of the medio-lateral axes and the knee center point.

Once the femoral head sphere SF with its center H1 and the femoral neck axis AX1 have been determined, a 3D mechanical femur coordinate system $(X_F, Y_F, Z_F)$ is constructed from the femur head center H1, the knee center K and the knee transverse axis ML that joins the points M and L which are the medial and lateral epicondyles of the knee or that joins the most posterior points of the knee condyles, as illustrated in FIG. 17. These last two anatomical elements are determined from 3D images acquired at the level of the knee joint as shown in FIG. 18. From these images, the knee center point K is determined. It is easy to find the centroid of these images after appropriate thresholding and compute an initial knee center K0. From that point, a rectangular box is computed around K0 in the axial image plane containing K0, such box being adjusted to be the smallest in contact with surface points detected on the bone. The center of the rectangular box becomes the estimation of the knee center K1. To refine even more the location of the knee center, it is further possible to extract the femur Medio-Lateral axis MLe as being the epicondylar axis in the knee 3D image. The epicondyles points E1 and E2 can be automatically detected by searching for example the two most distant bone points in the rectangular box computed above, passing within a given range of the knee center point K1. Other algorithms can be used to detect the epicondylar axis. Once this MLe axis has been determined, the knee center point K can be defined as the middle of the MLe segment. In another embodiment, a Medio-Lateral axis that we can extract is the postero-condylar axis MLp. It can be extracted using iterative methods to search for the most posterior points in the axial images of the knee.

Figure 19A:
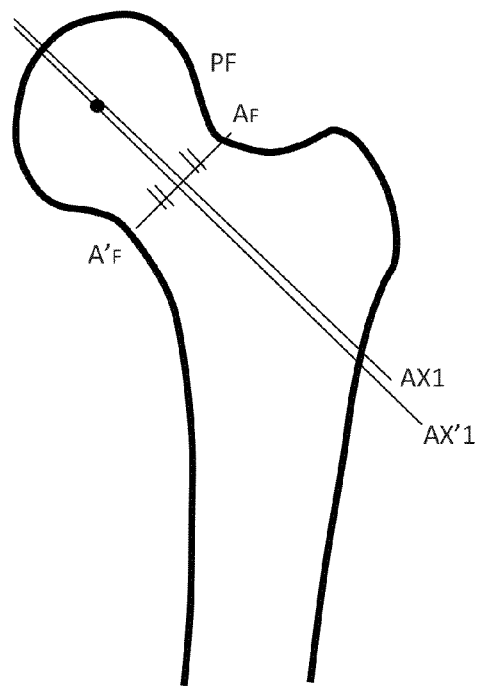
FIGS. 19A and 19B show two orthogonal radial cross-sectional views through the neck axis at 12 o'clock and 3 o'clock, in which the precise femoral neck is adjusted.
Figure 19B:
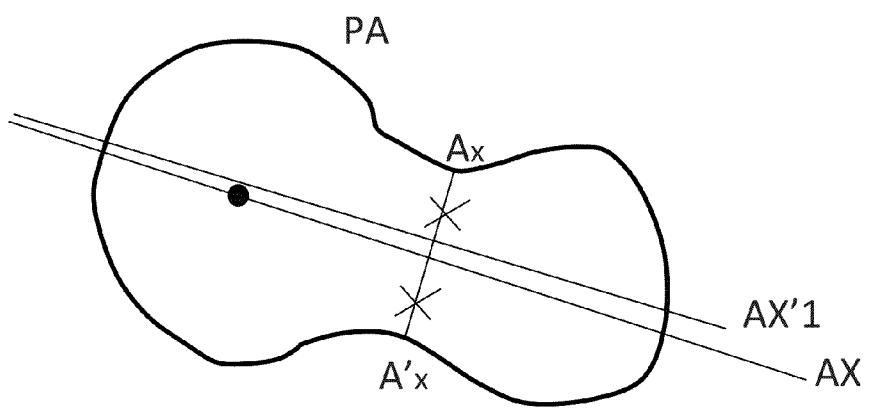

In a preferred embodiment, the final process of step S5 consists in adjusting the precise neck axis AX1 in two preferential radial planes as shown in FIGS. 19A and 19B. A pseudo frontal plane PF is determined in the 3D mechanical coordinate system of the femur as passing through the neck axis AX1 and the knee center point K. The knee axis AX1 is adjusted in the plane PF so that it passes in the middle of the shortest segment defined by the points Af and A'f computed on the intersection of the 3D surface model and the plane PF (FIG. 19A). Then a pseudo axial plane PA is determined in the 3D mechanical coordinate system of the femur as passing through the neck axis AX1 and orthogonal to the plane PF. The knee axis AX1 is then adjusted in the plane PA so that it passes in the middle of the shortest segment defined by the points Ax and A'x computed on the intersection of the 3D surface model and the plane PA (FIG. 19B). The axis AX represents the fully adjusted neck axis of the bone.

The method described above hence results in the accurate and reproducible determination of the precise center H1 of the femoral head, a precise radius R1 of the sphere adjusted to the femoral head, the orthogonal 3D mechanical coordinates system $(X_F, Y_F, Z_F)$ of the femur centred on H1, and the adjusted neck axis AX, from 3D medical image of the hip articulation.

In another preferred embodiment, the user can validate the precise neck axis resulting from one of the automatic computation described previously from a display of the resulting precise neck axis overlaying the 3D image of the bone. In case of failure of a valid precise neck axis determination, the user can manually determine in the two radial planes PF and PA the precise neck axis by adjusting the position and orientation of the line representing the neck axis in the two corresponding image slices.

These geometric elements can further be used to compute geometrical characteristics of the bone anatomy, such as the orientation of the neck axis AX in the coordinate system $(X_F, Y_F, Z_F)$, or the degree of deformity of the actual femoral head as a deviation volume from the adjusted sphere as described by Nötzli et al and Pfirrmann et al.

It can be easily understood from the man of the art, that the method of the invention can be implemented in a computer algorithm that will produce fast, automatic and reproducible computation of the femur geometric elements and the deduced geometric characteristics.

ADVANTAGES

The advantage of the invention is the precise, and automatic determination of critical characteristic elements of a bone in a 3D image requiring the least possible input from user interaction. From the determination of these elements, it is then possible to compute reliable measures characterizing the deformation of the bone. Usually those measurements are performed manually by a radiologist, which takes time and efforts and is prone to human errors or inaccurate measurements.

The invention claimed is:

1. An automated method for precise determination of the head center and radius and the neck axis of an articulated bone from acquired 3D medical image of an articulation, the articulation comprising two bones one of which is said bone with a head and a neck, the method comprising the following steps:
   i) determining automatically, from a 3D image of the bone having a head and a neck, an approximate sphere of the head of the bone defined by an approximate head center and an approximate radius, that substantially fits the spherical portion of the head of the bone;
   ii) constructing automatically from the 3D image and from the approximate sphere of the head of the bone, a 3D surface model of the bone;
   iii) determining automatically, from the 3D surface model of the bone and from the approximate sphere of the head of the bone, an approximate neck axis of the neck of the bone;
   iv) determining automatically, from the 3D surface model and from the approximate sphere of the head of the bone, a precise sphere defined by a precise head center and a precise radius of the head of the bone;
   v) determining automatically, from the 3D surface model, from the precise sphere of the head and from the approximate neck axis, a precise neck axis.

2. The method of claim 1, wherein the step of determining the approximate sphere comprises the following steps:
   a) defining from the 3D image of the bone having a head and a neck and from a threshold level which identifies level of cortical bone in medical images, a set of 3D connected components belonging to bone elements, and labelling these connected components with a label of the bone of the articulation they belong to, in order to identify the 3D connected components belonging to the bone with a head and a neck;
   b) determining from said 3D connected components, said approximate sphere of the head of the bone that substantially fits the spherical portion of the head of the bone.

3. The method of claim 2, wherein step a) is carried out by an automatic computation comprising the following steps:
   i) determining the lateral-medial, inferior-superior and antero-posterior orientations of the bone comprising a head and a neck from the knowledge of the orientation of the 3D image;
   ii) computing the 3D connected components for a high threshold level by applying standard thresholding and connecting operators;
   iii) labelling the connected 2D component detected in the most inferior slice of the 3D image as belonging to the bone comprising a head and a neck;
   iv) propagating the label of the connected 2D component in the most inferior slice, to the 3D connected component containing the 2D component.

4. The method of claim 2, wherein step b) is carried out by an automatic computation determining amongst candidate points in the 3D image, the point yielding the greatest spherical score, the spherical score being a ratio representing the likelihood of the candidate point to be the center of a sphere fitting the head portion of the bone, the spherical score also defining the radius value associated with the center.

5. The method of claim 4, wherein the spherical score is computed by the following steps:
   i) drawing a set of straight lines, each straight line diametrically extending from the approximate head center;
   ii) for each straight line, determining a pair of two intersection points positioned where the straight line intersects the 3D connected components of the bone with a head and a neck;
   iii) sorting all pairs of two intersection points into radius intervals depending on the distance separating the two intersection points of the pairs;
   iv) for each radius interval, counting the number of pairs in the radius interval;
   v) determining the spherical score for the candidate point as the ratio between the greatest number of pairs amongst all radius intervals and the total number of straight lines in the set of straight lines.

6. The method of claim 2, wherein step b) is carried out by an automatic computation comprising the following steps:
   i) determining a 4D Hough space in the space of spheres determined by four parameters defining a head center and a radius, and applying the associated 4D Hough transform to the 3D connected components of the bone with a head and a neck, thus computing a weight for each point of the 4D Hough space;
   ii) determining the approximate sphere as the point in the 4D Hough space with heaviest weight.

7. The method of claim 4, wherein the volume in which the approximate head center is searched for is reduced from the whole 3D connected components of the bone with a head and a neck to a portion of those 3D connected components, using a priori knowledge of the bone anatomy, and by applying a method comprising the following steps:
   i) determining a bounding box of the 3D connected components of the bone with a head and a neck;
   ii) splitting the bounding box of the 3D connected components in two parts by an antero-posterior plane passing through the middle of the bounding box, and keeping only the portion of the 3D components contained in the medial hemi-bounding box;
   iii) splitting the medial hemi-bounding box in two sub-parts by an infero-superior plane passing through the middle of the medial hemi-bounding box, and keeping only the portion of the 3D components contained in the superior medial hemi-bounding box;
   iv) computing an antero-posterior plane passing through the middle of the superior medial hemi-bounding box;
   v) computing spherical scores or 4D Hough transform respectively only along the segment passing through the middle of the antero-posterior plane, bounded by the superior medical hemi-bounding box.

8. The method of claim 4, wherein the user is asked to validate the resulting approximate sphere and wherein in case of failure of the automatic determination of a valid approximate sphere, step b) is carried out manually by designating in two orthogonal 2D slices selected in the 3D image of the bone an approximate head center point and drawing approximate circles over the head contours to determine an approximate sphere radius.

9. The method of claim 2, wherein the step of constructing the 3D surface model of the bone is carried out automatically by applying conventional surface generation operators from said segmented 3D connected components.

10. The method of claim 9, wherein if the used threshold is not differentiating enough to separate the 3D connected components of the bone with a head and a neck from the other bone of the articulation, the approximate sphere of the head of the bone is used to force the segmentation and the separation of the 3D connected components of the bone with a head and a neck from the other bone of the articulation before the generation of said 3D surface model, and the approximate sphere surface is used to complete generated said 3D surface model at the location of forced separation of the 3D connected components.

11. The method of claim 1, wherein the step of determining the approximate neck axis is carried out by an automatic computation comprising the following steps:
   i) tracing a defined number of hemi-lines, at regular intervals, from the approximate head center and in the directions contained in an inferior and lateral quarter of space of the 3D image, limited by a superior plane and a medial plane passing through the approximate head center;
   ii) determining for each hemi-line, a pair of intersecting points as the intersection of the hemi-line with the approximate sphere and with the 3D surface model of the bone;
   iii) selecting pairs of intersecting points whose relative distance is below a defined threshold and thus defining from the selected pairs of points, a 3D curve along the neck from the intersection points corresponding to the intersection of the hemi-lines with the 3D surface model of the bone;
   iv) computing a least-square plane from the points defining the 3D curve; the approximate neck axis being determined as the axis orthogonal to the least-square plane, passing through the approximate head center.

12. The method of claim 1, wherein the step of determining the approximate neck axis is carried out by an automatic computation comprising the following steps:
   i) tracing a defined number of hemi-lines, at regular intervals, from the approximate head center and in the directions contained in an inferior and lateral quarter of space of the 3D image, limited by a superior plane and a medial plane passing through the approximate head center;
   ii) determining for each hemi-line, an intersecting point as the intersection of the hemi-line with the 3D surface model of the bone, and selecting hemi-lines for which the distance between the approximate head center and the intersecting points is the longest, within a defined threshold;
   iii) computing for each selected hemi-line, radial planes rotating along the hemi-line at regular angulation interval, and computing the intersection curve of the 3D surface model of the bone and each radial plane;

iv) determining for each selected hemi-line, for each radial plane, a segment on the hemi-line by a minimum and a maximum distance from the approximate head center bounding the research area to the neck portion; and v) computing maximal distances from the segment to the intersection curve on both sides of the segment; the approximate neck axis being determined by the hemi-line associated with the smallest of the maximal distances.

13. The method of claim 11, wherein the user is asked to validate the resulting approximate neck axis, and wherein in case of failure of the automatic determination of a valid approximate neck axis, the determination of the neck axis is carried out manually by drawing lines approximating the neck axis in two orthogonal 2D slices selected in the 3D image of the bone.

14. The method of claim 1, wherein the step of defining the precise sphere is carried out by automatic computation of the following steps:

i) determining a spherical portion of the head surface defined by the approximate sphere and a plane orthogonal to the approximate neck axis and comprising the approximate head center, the spherical portion being opposite the neck with respect to the plane orthogonal to the approximate neck axis;

ii) determining a set of hemi-lines extending from the approximate head center, in the spherical portion of the head;

iii) determining a set of intersecting points on the 3D surface model of the bone, each intersecting point corresponding to the intersection between a hemi-line and the 3D surface model;

iv) fitting a precise sphere to the set of intersecting points by a least square method; the center of the precise sphere being the precise head center and the radius of the precise sphere being the precise radius of the head of the bone.

15. The method of claim 14, wherein the user is asked to validate the resulting precise sphere and wherein in case of failure of the automatic determination of a valid precise sphere, the determination of the precise sphere is carried out manually by designating in two orthogonal 2D slices selected in the 3D image of the bone a precise head center point and drawing precise circles over the head contours to determine a precise sphere radius.

16. The method of claim 1, wherein the step of defining the precise neck axis is carried out automatically by the following steps:

i) determining a 3D neck minimal curve on the 3D surface model of the neck portion of the bone;

ii) determining a least squares fitting plane to the 3D neck minimal curve;

iii) computing the orthogonal direction to the least squares fitting plane as the direction of the precise neck axis;

iv) computing the center of the projection of the 3D neck minimal curve on the least squares fitting plane as a point of the precise neck axis.

17. The method of claim 16, wherein the 3D neck minimal curve is determined by carrying automatically the following steps:

i) computing radial planes rotating along the approximate neck axis at regular angulation interval, and computing the intersection curve of the 3D surface model of the bone and each radial plane;

ii) determining for each radial plane, the minimum distances between the approximate neck axis and the intersection curve on both sides of the neck axis, and thus determining a pair of points on the 3D surface model; the set of pairs of points from all radial planes defining a minimal 3D curve on the 3D surface model of the neck portion of the bone.

18. The method of claim 17, further determining the 3D neck minimal curve by locally adjusting the 3D location of the points defining the 3D neck minimal curve comprising the following steps carried out automatically:

i) creating an energy function connecting contiguous points of the 3D neck minimal curve, as a sum of distance between contiguous points;

ii) minimizing the energy function by minimizing the distance between contiguous points.

19. The method of claim 1, wherein the step of defining the precise neck axis is carried out automatically by the following steps:

i) computing the sphere intersection curves of the 3D surface model and a set of spheres centered on the precise head center and with increasing radius, starting from the precise radius of the head of the bone to a defined maximum radius;

ii) computing for each sphere intersection curve, a plane orthogonal to the line passing though the head center and the barycentre of the intersection curve;

iii) computing further a plane intersection curve of the 3D surface model and the orthogonal planes, and computing the barycentre of the plane intersection curve;

iv) computing a least square fitting line, fitting the set of barycentre points from the set of plane intersection curves, and the precise head center; the fitting line determining the precise neck axis.

20. The method of claim 16, further comprising an automatic additional adjustment of the precise neck axis, computed by the following steps:

i) computing a radial frontal plane passing through the precise neck axis and the knee center point;

ii) adjusting the precise neck axis in the radial frontal plane so that the adjusted neck axis passes through the middle of the minimal segment joining two opposite points of the intersection curve of the 3D surface model and the radial frontal plane in a portion representing the neck of the bone;

iii) computing an radial axial plane orthogonal to the radial frontal plane and passing through the adjusted neck axis adjusted in the radial frontal plane;

iv) adjusting the precise neck axis in the radial axial plane so that the adjusted neck axis passes through the middle of the minimal segment joining two opposite points of the intersection curve of the 3D surface model and the radial axial plane in a portion representing the neck of the bone.

21. The method of claim 20, wherein the user is asked to validate the resulting precise neck axis, and wherein in case of failure of the automatic determination of a valid precise neck axis, the determination of the precise neck axis is carried out manually by drawing a line in two orthogonal 2D slices selected in the 3D image of the bone.

* * * * *